United States Patent [19]

Neri et al.

[11] Patent Number: 6,117,976
[45] Date of Patent: Sep. 12, 2000

[54] MANUFACTURE AND USE OF POLYPEPTIDES TAGGED USING BINDING MOLECULES

[75] Inventors: Dario Neri, Cherry Hinton; Gregory Paul Winter, Cambridge, both of United Kingdom; Claudia De Lalla, Milan, Italy

[73] Assignee: Medical Research Council, London, United Kingdom

[21] Appl. No.: 08/641,873

[22] Filed: May 2, 1996

Related U.S. Application Data

[63] Continuation of application No. PCT/GB94/02420, Nov. 4, 1994.

[30] Foreign Application Priority Data

Nov. 4, 1993 [GB] United Kingdom ............. 9322772
Mar. 25, 1994 [GB] United Kingdom ............. 9405927

[51] Int. Cl.$^7$ ............. C07K 1/00; C12P 21/08; C12P 21/06; G01N 33/53
[52] U.S. Cl. ............. 530/350; 530/387.3; 530/402; 435/7.1; 435/69.1
[58] Field of Search ............. 530/350, 387.3, 530/402, 300, 806, 807, 412; 435/69.1, 69.3, 69.7, 7.1; 424/134.1, 185.1; 436/543, 546

[56] References Cited

U.S. PATENT DOCUMENTS 5,498,538  3/1996  Kay et al. ............. 435/69.1

FOREIGN PATENT DOCUMENTS

WO 94/18318  8/1994  WIPO ............. C12N 15/09

OTHER PUBLICATIONS

Stofko–Hahn et al., "A single step purification for recombinant proteins," FEBS Letters, 302 (3):274–278, May 1992.

Beidler et al., "Cloning and High Level Expression of a Chemeric Antibody . . . ," Journal of Immunology, 141(11):4053–4060, Dec. 1988.

Jos A. Cox et al., "The Interaction of Calmodulin with Amphipilic Peptides," The Journal of Biological Chemistry, vol. 260, No. 4, pp. 2527–2534 (Feb. 25, 1985).

Kazuko Haga et al., "Synergistic Activation of a G Protein–coupled Receptor Kinase by G Protein βγ Subunits and Mastoparan or Related Peptides," The Journal of Biological Chemistry, vol. 269, No. 17, pp. 12594–12599 (Apr. 29, 1994).

Renata E. Stofko–Hahn et al., "A single step purification for recombinant proteins. Characterization of a microtubule associated protein (MAP 2) fragment which associates with the type II cAMP–dependent protein kinase," FEBS Letters, vol. 302, No. 3, pp. 274–278 (May, 1992).

Zhijun Luo et al., "Identification of the MAP2– and P75–binding Domain in the Regulatory Subunit (RIIβ) of Type II cAMP–dependent Protein Kinase," The Journal of Biological Chemistry, vol. 265, No. 35, pp. 21804–21810 (Dec. 15, 1990).

Tomio Ono et al., "Molecular Cloning Sequence and Distribution of Rat Calspermin, a High Affinity Calmodulin–binding Protein," The Journal of Biological Chemistry, vol. 264, No. 4, pp. 2081–2087 (Feb. 5, 1989).

Rasera Da Silva et al., "Hybrid myosin light chains containing a calcium–specific site from toponin C," Chemical Abstracts, vol. 116, No. 12, p. 354 (Mar. 30, 1992), abstract no. 123563g.

MacKenzie, et al., "Biofunctional fusion proteins consisting of a single–chain antibody and an engineered lanthanide–binding protein," Immunotechnology, 1:139–150, 1995.

Neri et al., "Calmodulin as a Versatile Tag for Antibody Fragments," Biotechnology, 13:373–377, Apr. 1995.

Primary Examiner—James C. Housel
Assistant Examiner—S. Devi
Attorney, Agent, or Firm—Marshall, O'Toole, Gerstein, Murray & Borun

[57] ABSTRACT

Molecules comprise (i) a polypeptide (such as calmodulin) which has calcium-dependent binding affinity for ligand and (ii) another polypeptide, the polypeptides preferably being joined by a peptide bond and produced by recombinant expression from a gene fusion. The molecules are useful in detection, immobilization, targeting and purification, cell-labelling, and band-shift assays for determining binding of a member of a specific binding pair (sbp) for complementary sbp member. For purposes of band-shift assays, polypeptide (i) need not have calcium-dependent binding affinity for a ligand, but should have a dissociation constant for a ligand of 10 nM or less, measured at a pH of between 6 and 9 at 20° C. In an alternative embodiment, a calmodulin-binding polypeptide which is, or is derived from, mastoparan is joined, as polypeptide (i) instead of a binding polypeptide, to the other polypeptide.

56 Claims, 13 Drawing Sheets

COOMASSIE BLUE STAINED GEL

GCATGCAAAT TCTATTTCAA GGAGACAGTC ATAATGAAAT ACCTATTGCC
SphI

TACGGCAGCC GCTGGATTGT TATTACTCGC GGCCCAGCCG GCCATGGCCC
                                         SfiI

AGGTGCAGCT GCAGGTCGAC CTCGAGATCA AACGGCGGC CGCAATCAAC
   PstI   SalI   XhoI        NotI

--------calm tag ------------------- stop -
CTGAAAGCTC TAGCCGCGCT GGCCAAAAAA ATCCTGTAAT AAGAATTC
                                      EcoRI

Fig.12.

Calmodulin sequence

```
M A D Q L T E E Q I A E F K E A F S L F
D K D G D G T I T T K E L G T V M R S L
G Q N P T E A E L Q D M I N E V D A D G
N G T I D F P E F L T M M A R K M K D T
D S E E E I R E A F R V F D K D G N G Y
I S A A E L R H V M T N L G E K L T D E
E V D E M I R E A D I D G D G Q V N Y E
E F V Q M M T A K
```

6,117,976

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
       (A) LENGTH: 24 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

Gln Ile Leu Trp Phe Arg Gly Leu Asn Arg Ile Gln Thr Gln Ile Arg
1               5                   10                  15

Val Val Asn Ala Phe Arg Ser Ser
            20

(2) INFORMATION FOR SEQ ID NO: 2:

(i) SEQUENCE CHARACTERISTICS:
       (A) LENGTH: 26 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

(2) INFORMATION FOR SEQ ID NO: 3:

(i) SEQUENCE CHARACTERISTICS:
       (A) LENGTH: 26 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 3:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

(2) INFORMATION FOR SEQ ID NO: 4:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 4:

Ile Asn Trp Lys Gly Ile Ala Ala Met Ala Lys Lys Leu Leu
1               5                   10

(2) INFORMATION FOR SEQ ID NO: 5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Val Asn Trp Lys Lys Ile Gly Gln His Ile Leu Ser Val Leu
1               5                   10
```

(2) INFORMATION FOR SEQ ID NO: 6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Ile Asn Leu Lys Ala Leu Ala Ala Leu Ala Lys Lys Ile Leu
1               5                   10
```

(2) INFORMATION FOR SEQ ID NO: 7:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Lys Arg Arg Ala Ile Gly Phe Lys Lys Leu Ala Glu Ala Val Lys Phe
1               5                   10                  15
Ser Ala Lys Leu Met Gly Gln Ala Met Ala Lys Arg Val Lys
                20                  25                  30
```

(2) INFORMATION FOR SEQ ID NO: 8:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Ile Lys Pro Ala Lys Arg Met Lys Phe Lys Thr Val Cys Tyr Leu Leu
1               5                   10                  15
Val Gln Leu Met His Cys Arg Lys Met Phe Lys Ala
                20                  25
```

(2) INFORMATION FOR SEQ ID NO: 9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Cys Glu Ile Lys Arg Ala Ala Ala Ile Asn Leu Lys Ala Leu Ala Ala
1               5                   10                  15

Leu Ala Lys Lys Ile Leu
            20

(2) INFORMATION FOR SEQ ID NO: 10:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 10:

Cys Glu Ile Lys Arg Ala Ala Ala Ile Asn Leu Lys Ala Leu Ala Ala
1               5                   10                  15

Leu Ala Lys Lys Ile Leu Ile Lys Arg Lys Arg Gln Gln
            20                  25

(2) INFORMATION FOR SEQ ID NO: 11:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 11:

Cys Glu Ile Lys Arg Ala Ala Ala Ile Asn Leu Lys Ala Leu Ala Ala
1               5                   10                  15

Leu Ala Lys Lys Ile Leu Ile Lys
            20

(2) INFORMATION FOR SEQ ID NO: 12:

(i) SEQUENCE CHARACTERISTICS:
            (A) LENGTH: 198 base pairs
            (B) TYPE: nucleic acid
            (C) STRANDEDNESS: double
            (D) TOPOLOGY: circular (ii) MOLECULE TYPE: Other nucleic acid: synthetic (xi) SEQUENCE DESCRIPTION: SEQ ID NO: 12:

GCATGCAAAT TCTATTTCAA GGAGACAGTC ATAATGAAAT ACCTATTGCC TACGGCAGCC      60

GCTGGATTGT TATTACTCGC GGCCCAGCCG GCCATGGCCC AGGTGCAGCT GCAGGTCGAC     120

CTCGAGATCA AACGGGCGGC CGCAATCAAC CTGAAAGCTC TAGCCGCGCT GGCCAAAAAA     180

ATCCTGTAAT AAGAATTC                                                   198

(2) INFORMATION FOR SEQ ID NO: 13:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (v) FRAGMENT TYPE: C-terminal (xi) SEQUENCE DESCRIPTION: SEQ ID NO: 13:

Glu Ile Lys Arg
1

(2) INFORMATION FOR SEQ ID NO: 14:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 14:

Ala Ala Ala Ile Asn Leu Lys Ala Leu Ala Ala Leu Ala Lys Lys Ile
1               5                  10                 15

Leu (2) INFORMATION FOR SEQ ID NO: 15:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 15:

Leu Glu Ile Lys Arg Ala Ala Ala Ala Ala Ile Asn Leu Lys Ala
1               5                  10                 15

Leu Ala Ala Leu Ala Lys Lys Ile Leu
                20                 25

(2) INFORMATION FOR SEQ ID NO: 16:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: Other nucleic acid: oligonucleotide primer (xi) SEQUENCE DESCRIPTION: SEQ ID NO: 16:

AGTTCCGCCA TAGCGGCCGC TGACCAACTG ACAGAAGAGC AG                               42

(2) INFORMATION FOR SEQ ID NO: 17:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: Other nucleic acid: oligonucleotide primer (xi) SEQUENCE DESCRIPTION: SEQ ID NO: 17:

ATCCATCGAG AATTCTTATC ACTTTGATGT CATCATTTG                                   39

(2) INFORMATION FOR SEQ ID NO: 18:

```
     (i) SEQUENCE CHARACTERISTICS:
         (A) LENGTH: 96 base pairs
         (B) TYPE: nucleic acid
         (C) STRANDEDNESS: double
         (D) TOPOLOGY: circular (ii) MOLECULE TYPE: Other nucleic acid: synthetic (ix) FEATURE:
         (A) NAME/KEY: CDS
         (B) LOCATION: 1..96

(xi) SEQUENCE DESCRIPTION: SEQ ID NO: 18:

TTA TTA CTC GCG GCC CAG CCG GCC ATG GCC CAG GTG CAG CTG CAG GTC      48
Leu Leu Leu Ala Ala Gln Pro Ala Met Ala Gln Val Gln Leu Gln Val
 1               5                  10                  15

GAC CTC GAG GAT CAA CGG GCG GCC GCT GAC CAA CTG ACA GAA GAG CAG      96
Asp Leu Glu Asp Gln Arg Ala Ala Ala Asp Gln Leu Thr Glu Glu Gln
                20                  25                  30

(2) INFORMATION FOR SEQ ID NO: 19:

(i) SEQUENCE CHARACTERISTICS:
         (A) LENGTH: 32 amino acids
         (B) TYPE: amino acid
         (D) TOPOLOGY: linear (ii) MOLECULE TYPE: protein (xi) SEQUENCE DESCRIPTION: SEQ ID NO: 19:

Leu Leu Leu Ala Ala Gln Pro Ala Met Ala Gln Val Gln Leu Gln Val
 1               5                  10                  15

Asp Leu Glu Asp Gln Arg Ala Ala Ala Asp Gln Leu Thr Glu Glu Gln
                20                  25                  30

(2) INFORMATION FOR SEQ ID NO: 20:

(i) SEQUENCE CHARACTERISTICS:
         (A) LENGTH: 149 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 20:

Met Ala Asp Gln Leu Thr Glu Glu Gln Ile Ala Glu Phe Lys Glu Ala
 1               5                  10                  15

Phe Ser Leu Phe Asp Lys Asp Gly Asp Gly Thr Ile Thr Thr Lys Glu
                20                  25                  30

Leu Gly Thr Val Met Arg Ser Leu Gly Gln Asn Pro Thr Glu Ala Glu
                35                  40                  45

Leu Gln Asp Met Ile Asn Glu Val Asp Ala Asp Gly Asn Gly Thr Ile
 50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
                100                 105                 110

Leu Gly Glu Lys Leu Thr Asp Glu Glu Val Asp Glu Met Ile Arg Glu
                115                 120                 125

Ala Asp Ile Asp Gly Asp Gly Gln Val Asn Tyr Glu Glu Phe Val Gln
                130                 135                 140
```

```
Met Met Thr Ala Lys
145
```

MANUFACTURE AND USE OF POLYPEPTIDES TAGGED USING BINDING MOLECULES

CROSS-REFERENCE TO RELATED APPLICATIONS

This is a continuation of International Application No. PCT/GB94/02420, filed Nov. 4, 1994, which in turn claims priority from Great Britain patent applications 9405927.6, filed Mar. 25, 1994, and 9322772.6, filed Nov. 4, 1993.

FIELD OF THE INVENTION

The present invention relates to detection, immobilization, targeting and purification of recombinant polypeptides. In particular it relates to the labelling or tagging of proteins with calcium-dependent binding molecules such as calmodulin, for example by creating fusion proteins, enabling use of the resultant molecule in the manners indicated.

BACKGROUND OF THE INVENTION

A number of different approaches have been taken to general methods of detection, immobilization, targeting and one-step affinity purification for recombinant proteins. The expression in bacteria of antibody fragments derived from monoclonal antibodies (Skerra, A. & Pluckthun, A., 1988 Science 240 1038–1041; Better, M. et al, 1988 Science 240 1041–1043) or from bacteriophage display repertoires (for review, see Winter, G. et al, (1994) Annual Rev. Immunol. 12 433–435) has reinforced the need for a widely applicable detection system. The initial demonstration that chimeric antibodies could be made where antibodies were fused to other proteins which retained their biological function (M. S. Neuberger & T. H. Rabbitts, 1984; UK patent 2,177,096B) opened the way to the construction of such genetic fusions with antibody molecules.

A variety of fusion tags have been used to date for recombinant proteins: (i) a peptide which recognizes a specific antibody e.g. the myc tag, (Munro, S., and Pelham, H. R. B. (1986) Cell, 46, 291–300; Ward, E. S., Gussow, D., Griffiths, A. D., Jones, P. T. and Winter, G. (1989) Nature, 341, 544–546); the Flag-peptide (Hopp, T. P. et al (1988) BioTechnology, 6, 1204–1210); the KT3 epitope (Martin, G. A. et al (1990) Cell, 63, 843–849; Martin, G. A., et al (1992) Science, 255, 192–194); an α-tubulin epitope (Skinner, R. H. et al (1991) J.Biol.Chem., 266, 14163–14166); the T7 gene 10 protein peptide tag (Lutz-Freyermuth, C., Query, C. C. and Keene, J. D. (1990) Proc. Natl. Acad. Sci. U.S.A., 87, 6393–6397) or an affinity support using poly-histidine tails binding to nickel-chelating agarose (Skerra, A., Pfitzinger, I. and Pluckthun, A. (1991) BioTechnology, 9, 273–278; Lilius, G., et al (1991) Eur. J. Biochem., 198, 499–504); the strep-tag, a peptide tag binding to streptavidin (Schmidt, T. G. M. and Skerra, A. (1993) Protein Engineering, 6, 109–122); (ii) a protein domain which forms a complex with a second (macro)molecule e.g. glutathione-S-transferase (Smith, D. B. and Johnson, K. S. (1988) Gene 67, 31–40); bovine pancreatic trypsin inhibitor, BPTI, (Borijin, M. and Nathans, J. (1993) Proc. Natl. Acad. Sci. U.S.A. 90, 337–341); maltose binding protein, MBP, (Bedouelle, H. & Duplay, P. (1988) Eur. J. Biochem. 171 541–549; Maina, C. V. et al. (1988) Gene 74 365–373), or (iii) a polypeptide sequence that can be biotinylated and thus made to interact with avidin or streptavidin (Schatz, P. J. (1993) Bio/Technology 11, 1138–1143).

Typically, some applications, (such as affinity purification) require a specific but low affinity interaction in order not to impair the function of the recombinant protein with a harsh elution protocol. Other applications (such as targeting and immobilization) require slow release and high-affinity binding of the tag. The known tag systems described above do not have this flexibility and although they perform well in many applications, each of them has some undesired draw-back.

Those tags recognized by specific monoclonal antibodies require columns which are either expensive or difficult to prepare. In some cases, harsh conditions are necessary to elute the bound protein (e.g. extreme pH values or chaotropic agents), which may impair the activity of the purified protein. Moreover, the affinity of the tag for the monoclonal antibody is usually not high enough for some applications, most notably for a stable immobilization of the tagged protein on a biosensor chip, e.g. for use with the BIAcore (Pharmacia).

The latter point applies also to the Strep-tag and perhaps to the polyhistidine tag, although stable immobilization on metal-chelating support might perhaps be achieved by high-density coating of the matrix. The polyhistidine tag has the draw-back that it does not allow protein detection, useful for example in ELISA (enzyme-linked immonusorbent assay) or immunoblot.

When the tag is a protein such as the BPTI tag, protein folding requirements of the tag itself, such as disulfide bridge formation, place limits on the possible applications. Furthermore, the high affinity of BPTI for trypsin ($K_d=6\times 10^{-14}$ M), makes elution of BPTI-tagged proteins from trypsin difficult.

Stofko-Hahn et al. ((1992) FEBS Lett. 302, 274–278) have made a fusion of a calmodulin-binding peptide tag derived from the C-terminus of rabbit skeletal muscle myosin light-chain kinase (SK-MLCK) and a recombinant protein and used this in purification on an affinity support.

SUMMARY OF THE INVENTION

Generally, the present invention provides molecules comprising a binding polypeptide and another polypeptide. There are a number of types of these molecules with various properties making them suitable for various uses, for example in purification of tagged proteins from affinity columns or by ion exchange chromatorgraphy, in band-shift assays and multimerisation. The binding of the binding polypeptide to ligand may be calcium-dependent. By this is meant that the dissociation constant for the ligand is reduced by the presence of calcium ions, that is binding is much stronger in the presence of calcium ions. For the applications described herein, it is preferred that this reduction is at least 10 fold when the binding protein has half of its calcium ion sites occupied. Preferably the dissociation constant is greater than 10 nM at a pH of between 6 and 9 at 20° C. and 10 nM or less in the presence of calcium ions, most preferably 1 nM or less. For some calcium-dependent binding proteins, other analagous ions may replace calcium, for example strontium.

In a one aspect the present invention provides a molecule comprising (i) a polypeptide able to bind a ligand with a binding affinity with a dissociation constant ($K_d$) of 10 nM or less, measured at a pH of between 6 and 9 at 20° C., and (ii) another polypeptide. So Preferably the dissociation constant is 1 nM or less. The binding affinity may be calcium-dependent, as discussed. Molecules with these characteristics are especially useful in band shift assays and multimerisation, as discussed further infra.

In another aspect the present invention provides a molecule comprising (i) a polypeptide ("calcium-dependent binding polypeptide") able to bind a ligand of calmodulin with a binding affinity which is dependent on the presence of calcium ions, and (ii) another polypeptide. As discussed herein, calmodulin (SEQ ID NO: 20) is ideally suited for use in purification of recombinant proteins, binding ligands with high affinity but capable of elution from affinity columns under mild conditions. Other calcium-dependent binding polypeptides able to bind ligands of calmodulin, such as mastoparan (SEQ ID NO: 6) and fragments and derivatives thereof, enjoy these same desirable properties and are useful in the same context. An example is troponin C.

For use in band-shift assays (discussed further infra), molecules according to the present invention should have not only a low dissociation constant (e.g. 10 nM or less and preferably 1 nM or less, measured at a pH between pH6 and pH9 at 20° C.), they preferably have a negative charge at about pH 8 of at least −5, preferably at least −10. The net charge of a protein at about pH 8 is defined by comparing the number of positively charged amino acid residues (lysines and arginines) with the number of negatively charged amino acids (glutamate and aspartate). If there are 10 more negatively charged residues than there are positively charged residues then the net charge is −10.

As discussed, preferred calcium-dependent binding polypeptides are calmodulin and troponin C. Fragments of these, retaining calcium-dependent binding for a ligand, may be used (as demonstrated herein), as may derivatives. The term "derivative" encompasses amino acid sequence variants with, for example, an insertion, deletion or substitution of one or more amino acids compared with wild-type, chimaeric fusion polypeptides and polypeptides modified post-translationally.

Molecules according to the present invention may comprise a binding domain of a member of a specific binding pair (sbp) such as an antibody or other polypeptide comprising an immunoglobulin binding domain. Other sbp members are discussed infra and still more will be apparent to those skilled in the art. Properties of binding of the sbp member to complementary sbp member (eg antibody to antigen) may be studied using a band-shift assay (wherein electrophoretic mobility is compared in the presence and absence of complementary sbp member) as provided herein.

For many purposes, molecules according to the present invention may be labelled using, for example, a fluorescer.

For some applications, the calcium-dependent binding polypeptide and ligand need to have a half-life which is long enough to allow employment of a multimer comprising the molecule and ligand. An example of where a reasonably long half-life is required is in a band-shift assay. The components of the multimer must remain bound together in a sufficient amount to allow detection following electrophoresis. Thus, the half-life of the multimer may be a minimum of around 15 minutes, but is preferably at least 60 minutes, at 20° C.

Multimers wherein the ligand is a polypeptide and is fused to another polypeptide may find a number of uses, dependent on the nature of that other polypeptide.

It is preferred that the molecules are produced by expression from nucleic acid comprising gene fusions, such that the components of the molecules are linked by a peptide bond. Nucleic acid encoding such molecules is provided by the present invention: it may comprise a promoter (e.g. in an expression vector) for expression of the polypeptide fusion within host cells. Host cells containing such nucleic acid may be grown in culture to cause or allow production of the fusion molecules. The "tag" may then be used in the isolation of the resultant recombinant polypeptide, with, e.g., elution from an affinity column or ion exchange chromatography. Elution may make use of a calcium-sequestrant/chelator, where the binding polypeptide has calcium-dependent binding affinity for the ligand employed.

Suitable vectors for expression can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known. A variety of different host cells are frequently employed by those skilled in the art, including bacteria, mammalian cells, yeast and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli.*

It should be noted that the term "fusion" is used herein in the context of joining of two polypeptides to form a molecule. The preferred mode of joining is via a peptide bond, so that a "fusion protein" may be produce by expression from encoding nucleic acid therefor. However, other modes of joining are envisaged. The term "fusion" should be understood to cover these unless the context requires otherwise.

Thus, the tag may be appended to another polypeptide by chemical modification or non-covalently. For instance, a cysteine group may be incorporated at the C-terminus of an sbp member such as a single chain Fv antibody fragment and a binding protein such as calmodulin coupled using the heterobifunctional crosslinker SPDP (N-succinimidyl-3-(2-pyridyldithio)propionate). For non-covalent linkage, peptides favouring formation of dimers such as leucine zippers (P. Pack and A. Pluckthun, *Biochemistry,* 31, 1579–1584, 1992) or fos and jun (*J. Immunol.* 148 1547–1553, 1992) may be appended to the two polypeptides to be linked. The complex forms on mixing of the proteins. This non-covalent coupling procedure may generate protein-calmodulin complexes which are insufficiently stable for some uses, such as band-shift assays or in vivo applications.

In the work leading to aspects of the present invention, we have shown that a number of advantages may arise from linking a $Ca^{2+}$-dependent binding polypeptide, such as calmodulin, to the recombinant protein and using a peptide as a soluble ligand. Thus, a system is provided enabling combination of high affinity binding and mild elution protocols in affinity purification using the binding molecule as a tag, eg for recombinant proteins, in particular recombinant antibodies. Moreover, the high affinity for peptide tags and unusual electrophoretic properties of the calmodulin domain make it suitable for a range of other applications.

Troponin C has suitable properties to be used as an alternative fusion partner instead of calmodulin. It allows mild elution from affinity columns, has a high affinity for peptide tags and has a strong negative charge. Other calcium-dependent binding proteins which are homologous to calmodulin having high affinity for peptide tags are also suitable, eg for mild elution. Suitability may be assessed by determining whether the binding protein binds a ligand of calmodulin, especially a polypeptide ligand of calmodulin such as mastoparan or a derivative of mastoparan.

Such fusions (e.g. with calmodulin) have advantages over other fusion partners in several specific assays. Herein, we disclose the use of recombinant calmodulin fusions in a band shift assay (which may be a gel retardation assay) which allows the study of affinities of recombinant proteins such as antibodies, particularly for protein ligands and the ranking according to affinity of, for example, antibodies expressed from clones from an antibody library. The use of polypeptide fusions in confocal microscopy and fluorescent activated cell sorting (FACS) is also illustrated. Moreover, the interaction between calmodulin (and other calcium-dependent binding polypeptides, as discussed) and peptide ligands provides a means of heterodimerisation of proteins, as illustrated by the assembly of an antibody-calmodulin fusion with a protein (maltose binding protein) tagged with a peptide ligand of calmodulin. Production of fusions of calmodulin and recombinant proteins by expression from-encoding nucleic acid is also disclosed.

Dimerisation, whether formation of homo- or heterodimers, or even heteromulimerisation may be used for instance in tumour cell killing or immunoscintigraphy applications.

Calmodulin is a small protein (149 amino acids), extremely well conserved between species and poorly immunogenic (VanEldik, L. J. & Lukas, T. J. (1987) *Methods Enzym.* 139, 393–405). The amino acid sequence of calmodulin is shown in FIG. 12 (SEQ ID NO: 20). It is very resistant to denaturation, even though it does not contain any disulfide bridge. Human calmodulin has a net 24 20 negative charges in the absence of calcium or 16 negative charges after calmodulin binding to four calcium ions. Several proteins, peptides and organic compounds bind to calmodulin with nanomolar or subnanomolar affinity (Vorherr, T., et al. (1993) *Biochemistry* 32, 6081–6088;Ikura, M., et al (1992) *Science,* 256, 632–638; Fisher, T. H. et al. (1987) *Biochemistry* 26, 8024; Benitez-King, G., et al (1993) *Life Sciences* 53, 201–207) in a process that can be inhibited by calcium chelators such as EGTA.

The small molecules which bind to calmodulin include calmidazolium and melatonin. Melatonin has a dissociation constant of 188 pM for calmodulin, but despite this high affinity is unsuitable for applications which require its complex with calmodulin to remain intact, such as band-shift assays and multimerisation. The low half-life of dissociation of melatonin from calmodulin means that no complex is detected on band shift assays (Example 11). Thus, a long half life of dissociation, in excess of the time required to perform the experimental procedure required, such as band shift assays, is an essential property of the detection complex in certain contexts.

Peptide tags such as those derived from mastoparan bind to calmodulin with suitable long half lives. The TAG peptides of Table 2 have off-rates of less than $10^{-4}$ $s^{-1}$.

Herein we also disclose a number of peptides which have not been used previously as tags for binding to recombinant calmodulin. Although these peptides, for example mastoparan have been shown to bind to calmodulin as free peptides, it was not obvious that they would bind in fusions since in the free form they were C-terminally amidated and had a free N-terminus., Mastoparan is the preferred peptide from which to derive designs for tag peptides. However, there are other peptides which bind with slightly lower, but nevertheless high affinity to calmodulin on which designs can be based, for example melittin, SK-MLCK (skeletal muscle myosin-light chain kinase derived peptide), NO-30 (a calmodulin binding peptide) and AC-28 (a calmodulin binding peptide) (Table 1; SEQ ID NOS: 3, 2, 7, & 8, respectively).

There are advantages arising from the unusual charge properties of calmodulin outlined above. The highly negatively charged calmodulin moiety causes the chimaeric protein to migrate towards the anode. The calmodulin tag allows the recombinant fusion proteins to be purified on anion exchange resins, and also direct the fusions to the anode in native polyacrylamide gels over a wide range of pH values facilitating gel retardation assays (D. W. Carr & J. D. Scott *Trends Biochem. Sci.* 17 246–250, 1992; P. Ramanujam et al *BioTechniques* 8 556–563, 1990). This has particular advantages when screening for example antibodies from phage libraries where the consistency of migration of the calmodulin fusions means that band shift assays can be set up directly to monitor supernatants from bacterial cultures as in Example 7, without necessitating purification. We also demonstrate that despite calmodulin being an intracellular protein, it can be expressed in a fusion with antibody fragments by secretion from bacteria.

In designing an antibody-antigen fusion, a computer model of an antibody-Fv fragment fused to calmodulin was built from the known three dimensional structures of the antibody HyHEL-10 (directed against hen egg lysozyme) and calmodulin. The scfv fragment of HyHEL10 and calmodulin were linked by a two residue peptide (Ala)$_2$ between the C-terminus of the VL domain and the N-terminus of calmodulin (FIG. 1) to place the binding sites for antigen and calmodulin ligands far enough apart to avoid interference between the sites. The similar three-dimensional structure of homologous proteins such as troponin C means they can be fused in a similar manner.

Calcium-dependent binding proteins suitable for use in various aspects of the present invention include calmodulin, troponin C, parvalbumin and oncomodulin.

[It should be noted that, unless the context requires otherwise, the term "antibody" is used herein to refer to whole antibody, any functional antibody fragment, or any polypeptide comprising an immunoglobulin binding domain, whether natural or synthetic. It has been shown that the function of binding antigens can be performed by fragments of a whole antibody. Example binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site; (viii) bispecific single chain Fv dimers (PCT/US92/09965) and (ix) diabodies, multivalent or multispecific fragments constructed by gene fusion—these are multimers of polypeptides, each polypeptide comprising a first domain comprising a binding region of an immunoglobulin light chain and a second domain comprising a binding region of an immunoglobulin heavy chain, the two domains being linked (eg by a peptide linker) but unable to associate with each other to form an antigen binding site: antigen binding sites are formed by the association of the first domain of one polypeptide within the multimer with the second domain of another polypeptide within the multimer (WO 94/13804).]

Fusion with a $Ca^{2+}$-dependent binding molecule (e.g. calmodulin) can provide a handle for purification of polypeptides such as antibodies or fragments thereof by anion exchange chromatography or by affinity chromatography on (e.g. calmodulin) antagonist columns. The fusions can be eluted under mild conditions with high salt from ion-exchange, or mildly with EGTA from calmodulin antagonist affinity columns. Other calcium chelators/sequestrants may be used for elution, for example EDTA (ethylenediaminetetraacetic acid) which is less selective than EGTA (ethylene glycol bis (6-aminoethylether)-N,N, N',N'-tetraacetic acid).

A site for cleavage by a specific protease may be incorporated between the recombinant protein and the calmodulin or other binding molecule. For instance, a site for cleavage by Factor Xa (EP 161937) or enterokinase (EP 035384) may be incorporated. This provides means for cleaving the recombinant protein from (e.g.) calmodulin if required for final application of the recombinant protein. Further it would also be possible to release recombinant protein from a calmodulin-ligand affinity column by treatment with Factor Xa (likewise other binding molecule fusion partners).

Furthermore the binding moiety can be readily detected by pre-incubation with fluorescent peptide ligands, as illustrated by the imaging of fluorescent bands-on gel electrophoresis, and cell surface antigens by confocal fluorescence microscopy and fluorescent activated cell sorting (FACS). In addition to fluorescein exemplified herein, other fluorescent reporter groups may be used, for example 7-nitrobenz-2-oxa-1,3 diazole (NBD), Texas red, coumarin or rhodamine.

Other highly sensitive methods for detection of calmodulin and other tags may be developed, for example by $Tb^{3+}$ luminescence after replacing $Ca^{2+}$ ions with $Tb^{3+}$ ions as recently described for oncomodulin (Clark, I. D., MacManus, J. P., Banville, D. & Szabo, A. G. (1993) *Anal. Biochem.* 210, 1–6). The preparation of a fusion protein between a single chain Fv fragment with oncomodulin has been reported with the purpose of enabling the labelling of the complex with $Tb^{3+}$ ions (R. Mackenzie et al, 4th IBC Conference on Antibody Engineering, San Diego, December 1993, Abstract 45).

Calcium-dependent binding proteins other than calmodulin may be used in systems disclosed herein, as long as they are able to bind labelled tags (such as the labelled TAG peptides of Table 2). For instance, troponin C, C-terminal fragments of calmodulin or mutants (amino aced sequence variants) of calmodulin may be used. Indeed, it has been shown that the TAG peptide binds well to troponin C (Example 10). Troponin C has a net negative charge of -27 at neutral pH and thus will tend to make fusions migrate towards the anode. Other calcium binding proteins, which may be homologous to calmodulin, such as calcineurin, oncomodulin and parvalbumin, may be screened for ability to bind suitable molecules such as mastoparan derived tag peptides, and their electrophoretic behaviour examined to determine their suitability for use in band shift assays. As discussed, for use in such assays high affinity binding and an off-rate such that there is not significant dissociation during electrophoresis are required.

C-terminal fragments of calmodulin (e.g. amino acids 81–149 (SEQ ID NO: 20) bind mastoparan-derived peptide tags and may be used in, for example, band-shift assays, as shown in Example 10. Mutants, derivatives and variants of calmodulin and other binding molecules may be used as long as they retain binding affinity for the tag (e.g. mastoparan). The C-terminal domain of troponin C (amino acids 94–162) may be usable. In contrast, the N-terminal domain of calmodulin does not bind the TAG peptides (Example 10).

Calmodulin fusions allow convenient detection of complexes, eg antibody-antigen, by band shift on gel electrophoresis (FIG. 5), a technique originally employed for studying protein-DNA interactions (Muller, M., et al. (1988) *Embo J.* 7, 4299–4304; Carey, J. (1988) *Proc. Natl. Acad. Sci. U.S.A.* 85, 975–979). The highly acidic nature of calmodulin (net charge -25 at pH 7.0) helps ensure that (for example) both the antibody fusion and the complex with antigen move toward the anode, even with highly basic antigens such as HEL as shown in example 7 (FIG. 5). A highly sensitive fluorescent gel imager allows the detection of subnanomolar concentrations of the fusion protein, and its complex with antigen (FIG. 5). Complex formation is even detectable using calmodulin fusions in bacterial extracts (FIG. 5). However, the antigen-antibody complexes presumably need to be stable (as with HyHEL-10 and MFE-23), with half-lives longer than the time taken for gel electrophoresis (15 min). The half-life of the complexes between calmodulin and the peptide tags described in this invention are well in excess of that needed for the native gel electrophoresis.

The band shift assay system, where the use of calmodulin fusions and peptide tags allows study of the relative affinity of members of specific binding pairs, such as antibodies with antigens, may be used with other fusion partners and labelled detection polypeptides. For example, the calmodulin/mastoparan pair may be replaced with thrombin/hirudin (T. J. Rydel et al, *Science* 1990, 249, 277–280; E. Skrzypczak-Junkun et al, *J. Mol. Biol.* 1991, 221 1379–1393); bovine pancreatic trypsin inhibitor/trypsin (Borijin and Nathans, 1993, supra) or barnase/barstar (Buckle et al, *Biochemistry* 1994, 33 8878–8889). It is preferable that the fusion partner for the antibody defines the electrophoretic characteristics of the antigen in a similar way to calmodulin, due to having a negative charge of at least -5 at about pH 8 and preferably greater than -10 at about pH 8. The fusion partner should have a high affinity for its complementary tag and there is a slow-off rate for the binding interaction so that the enough complex remains intact throughout electrophoresis.

Thus, troponin C is also a suitable fusion partner to use with mastoparan-derived tags. Hirudin, like calmodulin, provides a negatively charged partner which favours migration towards the anode. Hirudin, however, has the disadvantage compared with calmodulin that the hirudin contains disulphide bonds which are likely to reduce the efficiency of expression in bacteria. In contrast, it is shown herein that calmodulin fusions can be expressed efficiently in bacteria. Further, the hirudin/thrombin has the disadvantage that the thrombin molecule is much larger (288 amino acids) than calmodulin, making it more difficult to distinguish complexed from uncomplexed sbp members. Possible tags for this system include hirudin (65 amino acids) hirulog 1 (20 amino acids) and hirulog-1 (12 amino acids).

Thus, a scheme for band shift assay may be written as follows:

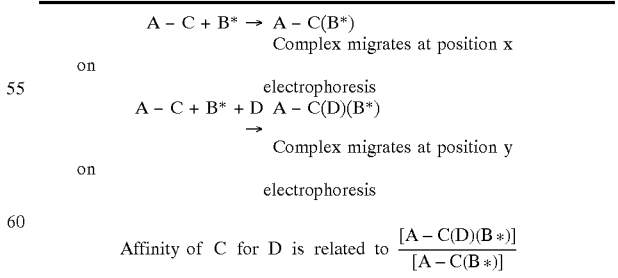

where C and D represent specific binding pair (sbp) members under study (eg C is an antibody fragment and D is an antigen), A is the fusion partner for the sbp member under study (eg calmodulin), A-C is the fusion polypeptide, B is the molecule which binds the fusion partner, eg a mastoparan-derived peptide tag. B* is B labelled, eg, with fluorescein.

Alternatively, A could be labelled (A*) and B unlabelled.

Hirudin/thrombin are alternatives for A and B and peptide hormones/receptors are alternative sbp members C and D which could be studied.

The principles of the use of binding molecule fusion in the study of antibody-antigen binding pairs is applicable also to other specific binding pairs, for instance peptide hormones/ receptors, transcriptional activators/DNA binding domains and cell surface signalling molecules such as T-cell receptors/MHC complex.

Thus, a further aspect of the invention provides a band-shift assay method for determining binding affinity of the binding domain of a member of a specific binding pair for a complementary sbp member of interest, the method comprising binding a binding polypeptide of a molecule according to the invention to a labelled ligand and comparing electrophoretic mobility of the resultant multimer in the presence and absence of the complementary sbp member. The binding polypeptide should be able to bind ligand with a binding affinity with a dissociation constant ($K_d$) of 10 nM or less, measured at a pH of between 6 and 9 at 20° C. The binding affinity may be dependent on the presence of calcium ions. As discussed, the half-life of the multimer is preferably at least about 15 minutes, most preferably at least about 60 minutes.

The strong binding interactions between calmodulin and peptide ligands also provide a means of creating dimers, or higher multimers. Dimeric peptide ligands were found to dimerise the antibody-calmodulin fusions (not shown); presumably multimeric peptide ligands would be capable of producing antibody multimers. Peptide tags were also used to create heterodimers; thus antibody fused to calmodulin was able to associate with MBP tagged with the calmodulin-binding peptide (Example 9; FIGS. 8A and 8B). Although the tag was stable when attached to MBP (expressed inside the bacteria), it was rapidly proteolysed when appended to secreted antibody fragments. For some applications it may therefore be desirable to design protease resistant tags.

This might be done by fusing derivatives of peptides where random amino acids have been incorporated at potential cleavage sites, for instance the two amino acids KK. These variable peptides could be fused to a single chain Fv and displayed on phage (WO92/01047) and phage could then be selected by binding to calmodulin. Peptide tags which are more resistant to protease activity and retain affinity for calmodulin may be selected. The phage display process should enrich for these.

Thus, a still further aspect of the invention provides multimers as disclosed herein, with a binding polypeptide fused to another polypeptide and the binding polypeptide non-covalently bound to ligand. The ligand may be a polypeptide fused to another polypeptide.

Antibody-calmodulin fusions have potential for in vivo use. Calmodulin is poorly immunogenic (VanEldik & Lukas, 1987 supra.), and it has been shown that calmodulin is not toxic, does not accumulate selectively in any organ and is rapidly excreted in the urine. In principle, for immunoscintigraphy antibody calmodulin fusions could be targeted to tumour cells, and detected by radioactively labelled calmodulin ligands. Indeed small specific ligands appear to detect tumours well (Kalofonos, H. P., (1990) *J. Nucl. Med.* 31, 1791–1796; Paganelli, G., et al. (1991) *Cancer Res.* 51, 5960–5966). A tag system as disclosed herein may be used instead of the established avidin-biotin system. Alternatively the antibody calmodulin fusion could be used to recruit effector functions to the tumour, for example another antibody fragment binding to cytotoxic T lymphocytes.

For in vivo applications, for example, multimeric complexes may be formed. For instance, to recruit cytotoxic T lymphocytes to tumour sites an antibody-calmodulin fusion directed against a tumour may be complexed with an antibody-mastoparan peptide fusion, and used for in vivo tumour killing. Alternatively, a two-stage process may be used where the anti-tumour fusion is injected and binds to the tumour and subsequently the anti-T cell fusion is added. If the second fusion is instead labelled with an isotope a similar system may be used for immunoscintigraphy.

In addition to use of calmodulin or other ligand-binding polypeptide as a "tag" in the numerous ways disclosed herein, the format may be reversed so that the "tag" is a calmodulin-binding polypeptide (which may be referred to as a peptide). The polypeptide may be mastoparan or a polypeptide derived from mastoparan. Preferred such polypeptides are shown in Table 2 (SEQ ID NOS: 6, 9, 10, & 11). Derivatives which retain calmodulin-binding ability may be used. Thus, mastoparan or a mastoparan derived polypeptide may be joined, eg by a peptide bond, to another polypeptide, which may comprise a binding domain of a member of a specific binding pair (e.g. an immunoglobulin binding domain) and used in purification, isolation, labelling, assaying and other ways disclosed herein and discussed at length supra e.g. for "tagging" with calmodulin.

Various aspects and embodiments of the present invention are illustrated in the following examples with reference to the figures. Further aspects and embodiments of the present invention will be apparent to those skilled in the art.

All documents mentioned in the text are incorporated by reference.

BRIEF DESCRIPTION OF THE FIGURES

FIG. 12: amino acid sequence of calmodulin (SEQ ID NO: 20).

DETAILED DESCRIPTION

EXAMPLE 1

Figure 1:
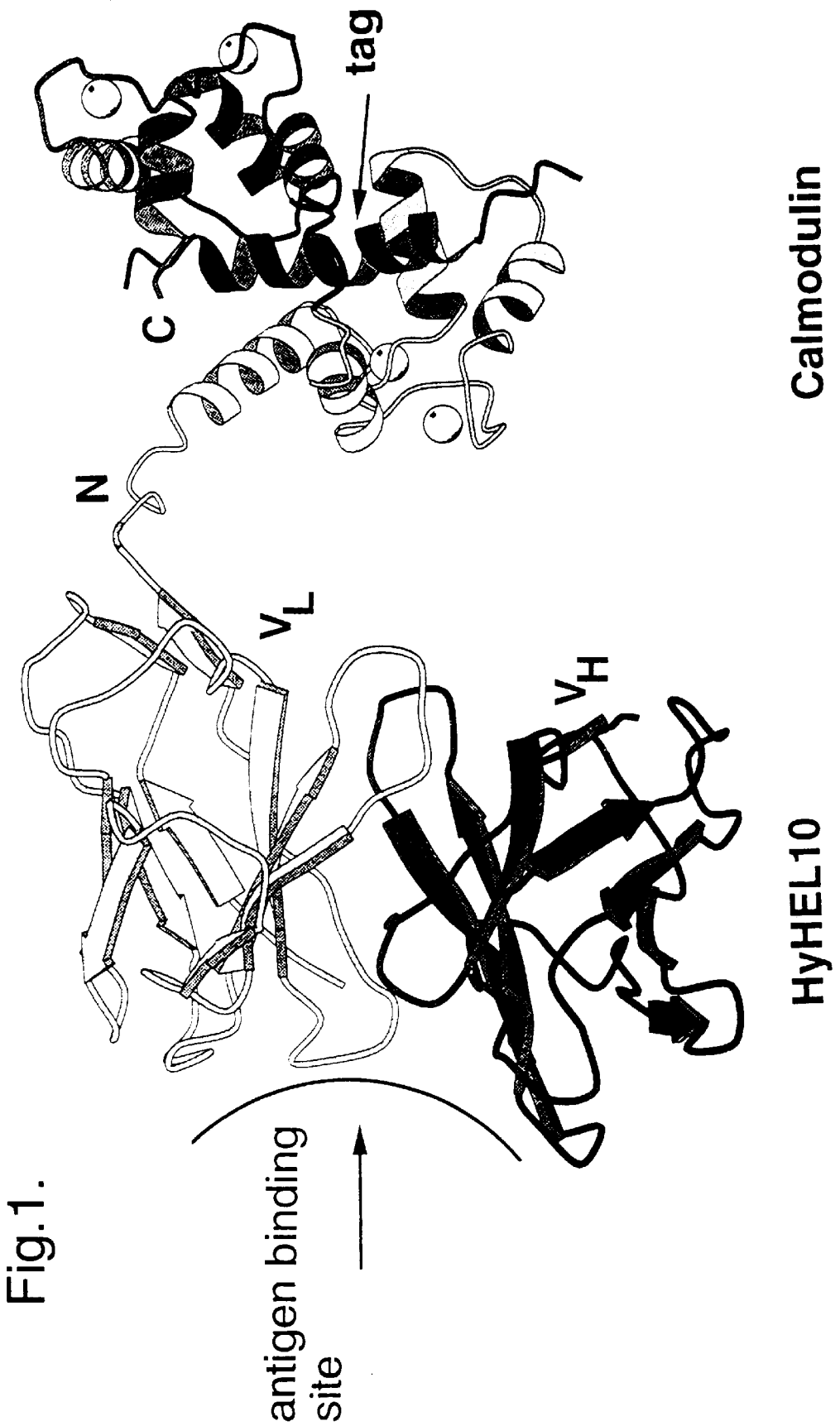
FIG. 1: HEL in complex with HyHEL-10 Fv fragment fused to calmodulin. Modelled by MOLSCRIPT (Kraulis, P. (1991) *J. Appl. Cryst.* 24, 946–950).

Evaluation of calmodulin-binding peptides as tags.

Table 1 shows the alignment of homologous peptide sequences which bind to calmodulin with high affinity ($K_a > 5 \times 10^7$ M$^{-1}$; Ikura et al., 1992, et. supra; Malencik, D. A. and Anderson, S. R. (1983) *Biochem. Biophys. Res. Comm.*, 114, 50–56) (SEQ ID NOS: 1–8). Amongst them, mastoparan (SEQ ID NO: 6) has the shortest sequence (14 amino acid residues) and the highest affinity ($K_a = 3.3 \times 10^9$ M$^{-1}$), and was the best candidate for the development of the calmodulin binding peptide tag.

The structure of the calmodulin/SMLK-peptide (Ikura et al., 1992, et. supra) was used to model mastoparan binding to calmodulin. The homology between mastoparan and SMLK-peptide sequences (Table 1) and preliminary NMR data, which revealed that mastoparan makes contacts with both N-terminal and C-terminal domain of calmodulin. The structure is reminiscent of a stick (mastoparan) in a doughnut (calmodulin).

Some potential problems became immediately apparent from the mastoparan sequence (Table 1; SEQ ID NO: 6), if it is to be used as a tag. Firstly, the mastoparan C-terminal carboxyl group is amidated. It was necessary to ascertain whether mastoparan in the deamidated form (i.e. with a free carboxylate group at the C-terminus) still binds to calmodulin with high affinity, and whether binding is still preserved when the C-terminus is extended with other peptide sequences. If this were the case, then mastoparan could be used as N-terminal tag, fused to the protein of interest. To use the tag at the C-terminal extremity of the protein it is necessary to ascertain whether the positively charged—NH3+moiety could be replaced by a foreign peptide sequence.

EXAMPLE 2

Evaluation of the requirement for free N- and C-termini in the mastoparan-derived tag Four peptide analogues of the mastoparan sequence were synthesized to investigate the requirement for free N- and C-termini in binding to calmodulin. These are shown in Table 2 (SEQ ID NOS: 9–11). All contain a cysteine as functionalization site and the C-terminal sequence of antibody $V_L$ domain (EIKR) (SEQ ID NO: 13) followed by the AAA tripeptide encoded by the NotI restriction site sequence, followed by mastoparan. The four peptides have different C-termini: —COOH, —CONH$_2$ and two peptide sequences derived from the calmodulin-binding peptide melittin.

The four peptides TAG-1 to TAG-4 (SEQ ID NOS: 9–11) were fluoresceinated, then complexed with a slight excess of calmodulin and run into a native gel. The peptide-calmodulin complex formation was observed both by fluorescent imaging of the gel (detecting peptide) and by coomassie-blue staining (detecting calmodulin). Comigration of fluorescent peak and coomassie-blue stained band indicates the formation of a stable peptide-calmodulin complex.

Peptide synthesis and modification.

Solid phase peptide synthesis was carried out on a model 350 multiple peptide synthesizer (Zinsser Analytic, Frankfurt, Germany), using Fmoc/t-butyl protecting group chemistry. Removal of the Fmoc groups was by treatment with 20% (v/v) piperidine in dimethylformamide and successive amino acid residues were added as N-hydroxybenzotriazole esters. Side-chain deprotection and cleavage from the resin was by 93% trifluoroacteic acid/3% 1,2-ethanediol/2% thioanisole/2% water. Peptides were tested for homogeneity by resolution on a Vydac C18 column (10 mM, 100×250 mm) and checked by amino acid analysis (PICO TAG, Waters, Milford, Mass., USA).

Peptide fluoresceination

For peptide fluoresceination, 1 mg of each peptide was dissolved in 1 ml of 100 mM NaHCO3, pH 8.9. One volume of peptide was mixed with one volume of water and 2 volumes of 2 mM iodoacetamidofluorescein (Molecular Probes Inc.) in dimethylformamide. The reaction was allowed to proceed for 15 minutes then quenched by adding dithiothreitol to 10 mM final concentration. The fluoresceinated peptides were separated from unreacted fluorescein using a Millipore MEM-SEP cartridge column (TBS= loading and wash buffer; TBS+0.5 M NaCl=elution buffer).
Native gel electrophoresis.

A 20 μl reaction was set up containing ca. 0.4 μg of fluoresceinated peptide and 18 μg of calmodulin (Sigma) in TBS containing 1 mM $CaCl_2$ (TBS is 50 mM Tris-HCl, pH 7.4, 100 mM NaCl in water). 7 μl of native gel mix (50% glycerol+0.05% bromophenol blue) were added, and 8 μl of each reaction resolved on a 15% native polyacrylamide gel at 150V, 15° C. The gel was first imaged on a U.V transilluminator and photographed, then stained with coomassie blue and photographed again.

Figure 9A:
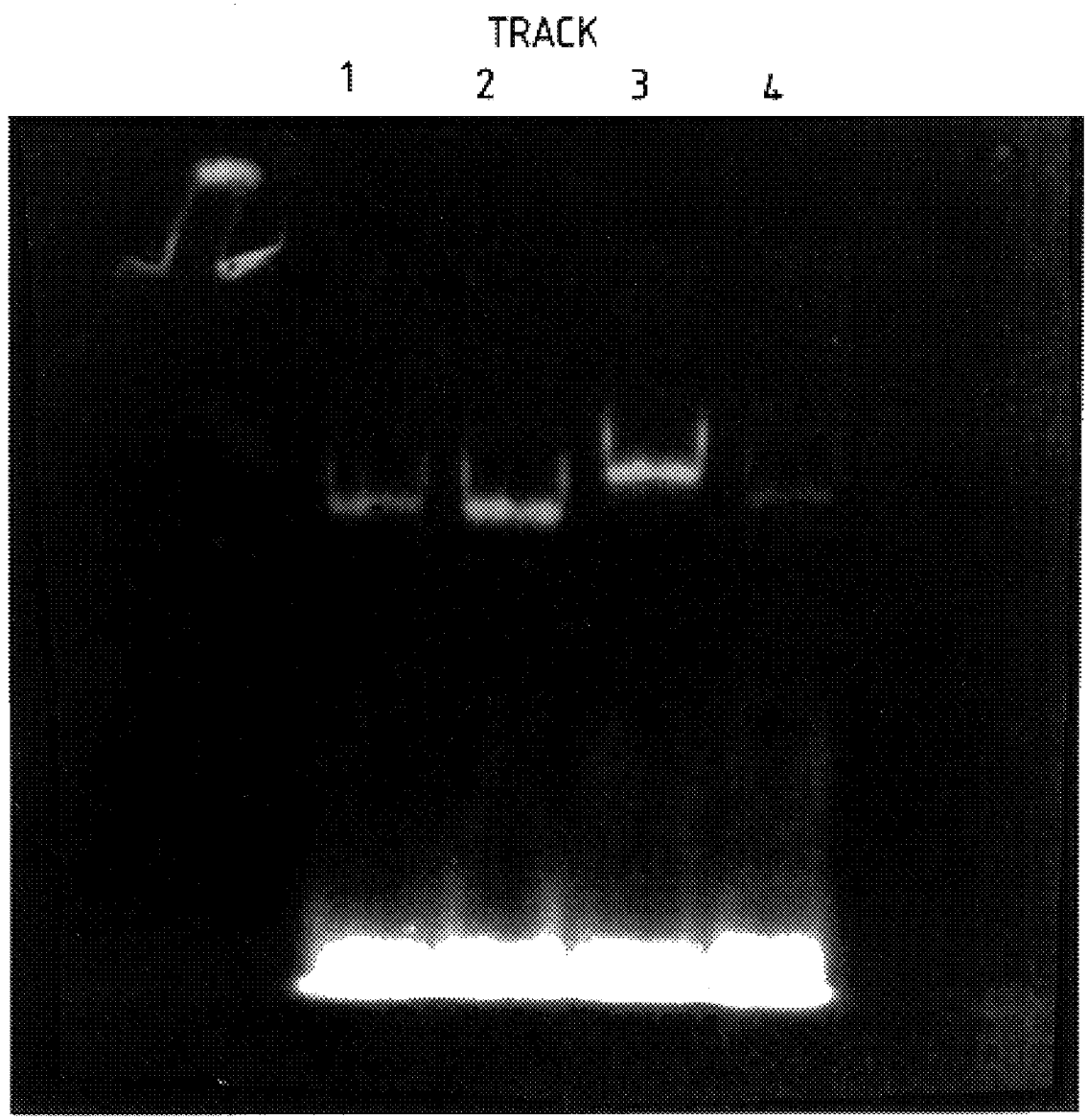
FIGS. 9A and 9B: Fluorescent and Coomassie blue detection of fluorescent peptide/calmodulin complexes. Native gel electrophoresis of calmodulin and fluoresceinated TAG1 (Track 1), calmodulin and fluoresceinated TAG2 (Track 2), calmodulin and fluoresceinated TAG3 (Track 3), and calmodulin and fluoresceinated TAG4 (Track 4). The gel was first imaged on a UV transilluminator and photographed (FIG. 9A) and then stained with Coomassie blue and photographed (FIG. 9B).
Figure 9B:
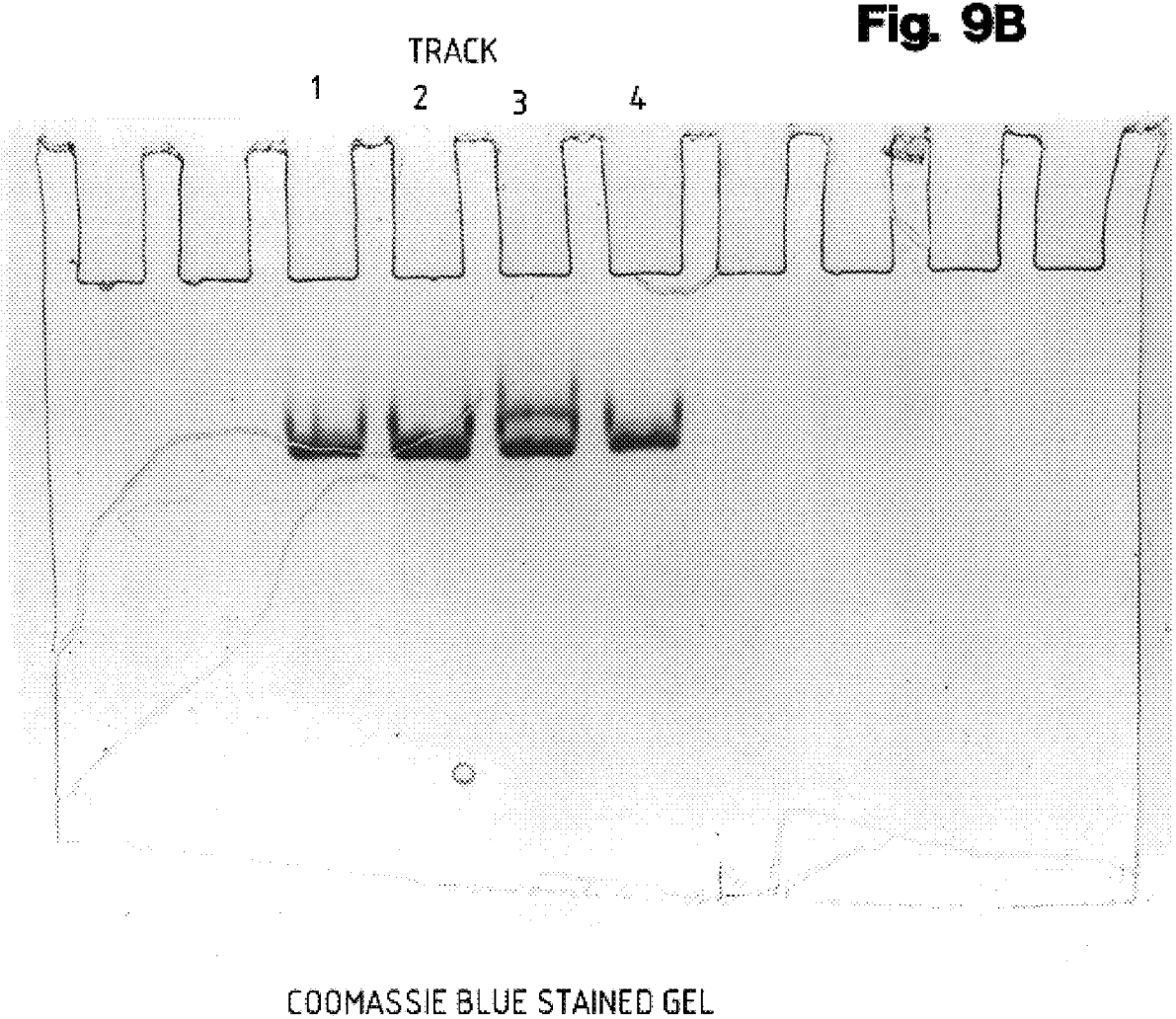

The result is shown in FIGS. 9A and 9B with FIG. 9A showing the gel photographed under UV fluorescence, and FIG. 9B showing the gel stained with Coomassie blue. Tracks 1, 2 & 4 show calmodulin complexed with TAG-1, 2 & 4 respectively. The fluorescent and coomassie blue tracks coincide, indicating the presence of peptide in stable complex with calmodulin. In track 3 (TAG-3+calmodulin) two bands are evident on coomassie staining and it is the upper of these that has bound peptide wheras the lower is free calmodulin. The mobility of the TAG-3+calmodulin complex differs from the previous two samples because of the positively-charged C-terminal extension; the free calmodulin band is visible because calmodulin is provided in excess in this experiment.

From this experiment, it was concluded that both N- and C-termini of the peptide sequence can be extended without preventing binding to calmodulin. This indicates that the mastoparan derived tags are an appropriate ligand for detection, purification and immobilisation of macromolecules, whether placed at either end or within the molecule of interest.

EXAMPLE 3

Purification of antibody single-chain Fv fragment fused with TAG peptide using calmodulin-agarose.

This example describes the construction of genetic fusions between mastoparan-derived TAG peptide tags and recombinant proteins and their purification on calmodulin agarose.

Figure 10:
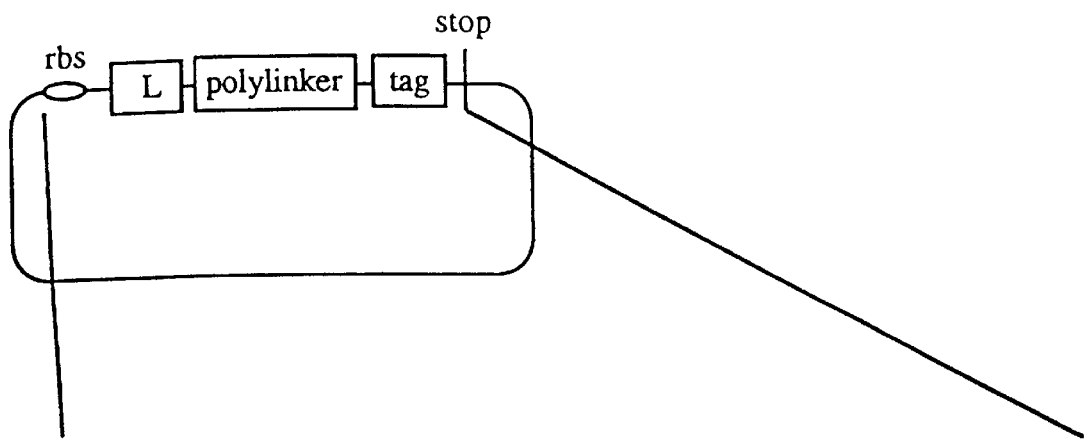
FIG. 10: Map of vector pDN123.

The expression vector pDN123 depicted in FIG. 10 was constructed. This vector was designed for expression of soluble proteins in *E.coli*, appending mastoparan-derived TAG peptides at the C-terminal extremity of the protein of interest. The peptides incorporated are AAA-INLKALAALAKKIL (SEQ ID NO: 14) when cloning at the NotI site and LEIKR-AAA-AAA-INLKALAALAKKIL (SEQ ID NO: 15) when cloning at the XhoI site. Single-chain Fv antibody fragment (scFv) encoding the anti-Hen egg-white lysozyme antibody D1.3 was cloned into this vector as an Sfi I-Not I fragment to produce plasmid pDN124 and transformed into *E.coli* TG1.

Growth and expression of soluble antibody.

TG1 cells containing plasmid pDN124 were grown overnight at 30° C. in 50 mls of 2× YT medium (2× YT is per liter; 16 g Bacto-tryptone, 10 g bacto-yeast extract, 5 g NaCl) containing 1% glucose and 100 μg/ml ampicillin. This culture was added to 500 ml of fresh medium of the same composition in a 2.5 liter glass conical flask and grown with rapid shaking for 1 hour at 30° C. The cells were then pelleted by centrifugation at 5,000× g, 10° C. for 10 minutes, the supernatant decanted and the cell pellet resuspended in 500 ml of 2× YT containing 1 mM IPTG (isopropyl thiogalactopyranoside) and 100 μg/ml ampicillin. The cells were returned to the 2.5 liter conical flask and grown with rapid shaking for 3 hours at 30° C.

Extraction of periplasmic proteins.

Cells were pelleted as above, and resuspended in 10 ml of PBS (PBS is per liter of water: 8 g NaCl, 0.2 g KCl, 1.44 g $Na_2HPO_4$, 0.24 g $KH_2PO_4$, adjusted to pH 7.4 with HCl) containing 1 mM EDTA. After 15 minutes incubation on ice the extracts were centrifuged at 10,000× g, 4° C. for 15 minutes, and the supernatant recovered. $CaCl_2$ was added to 10 mm final and the extract centrifuged at 20,000× g, 4° C. for 15 minutes, and the supernatant applied at a rate of 1 ml/min to a 10 ml bed volume calmodulin-agarose column (Sigma) pre-equilibrated in TBS+1 mM $CaCl_2$. The column was washed firstly with 20 mls of TBS+1 mM $CaCl_2$ then with the same buffer made to 0.4M with NaCl until the optical density of the flowthrough at 280 nM was less than 0.01. The antibody was eluted TBS+1 mM EGTA. Yield of scFv was ca. 5 mg from 500 mls.

Figure 11:
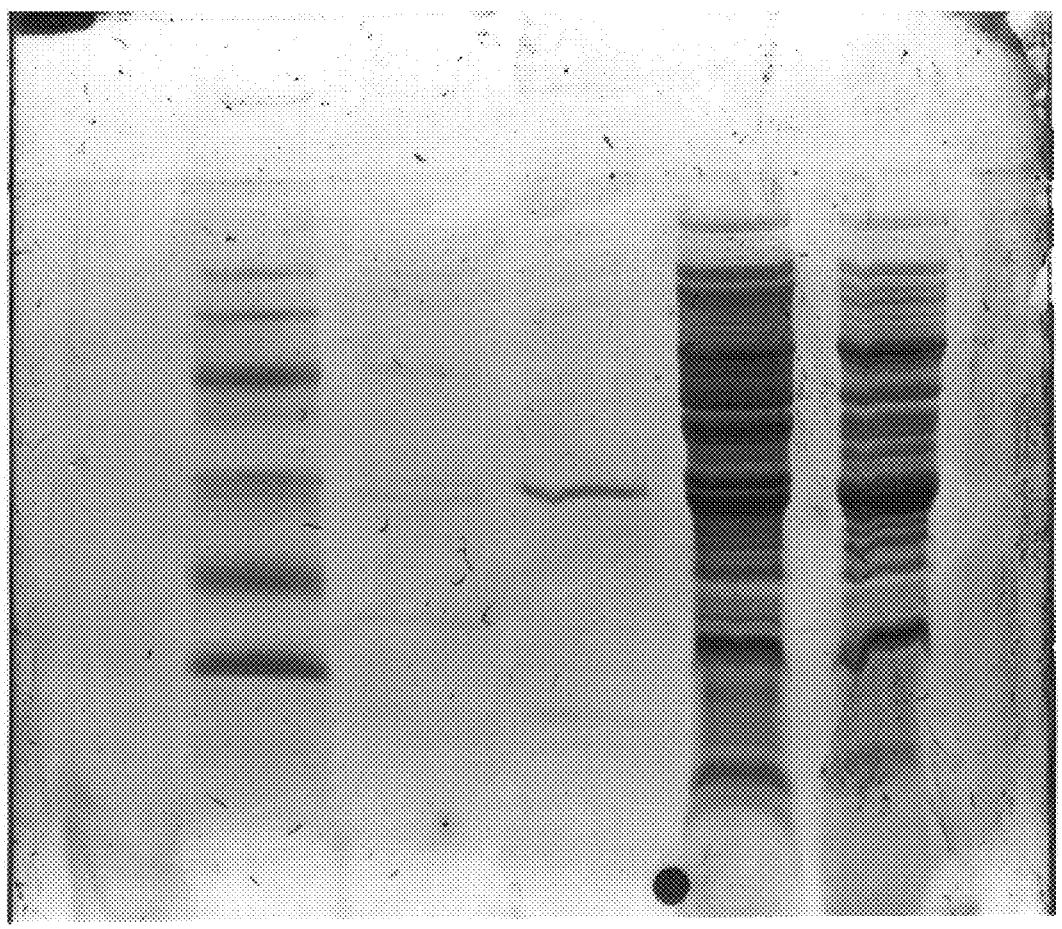
FIG. 11: SDS-polyacrylamide gel on samples from the purification of TAG-1 tagged scFvD1.3 from pDN124.

FIG. 11 shows a SDS-polyacrylamide gel of the results of the purification of scFv(D1.3) from pDN124. Lane 1 shows the molecular weight calibration marker bands (size expressed in kiloDaltons). In lane 4 and 5, periplasmic preparations of scFv(D1.3) without and with the C-terminal TAG peptide tag were run. The corresponding protein(s) retained on calmodulin-agarose column and subsequently eluted, were run in lane 2 and 3. It is evident that the system allows the one-step purification of proteins fused with the TAG peptides (lane 3) from complex protein mixtures (lane 5).

EXAMPLE 4

Binding of calmodulin to the scFv-TAG peptide fusions as detected using BIACore

A BIACore microsensor chip (Pharmacia) was coated with hen egg lysozyme to high surface density. scFv (D1.3) anti-lysozyme antibody fragments fused to the TAG peptide were purified on calmodulin columns or from periplasmic extracts were then examined for calmodulin binding. Both calmodulin-purified antibody and antibody from periplasmic extracts showed typical D1.3 lysozyme binding behaviour. In each case, calmodulin (in Tris buffered saline containing 0.1 mM $CaCl_2$) was passed over the chip. Calmodulin binding to the TAG peptide fusion was observed and the apparent off-rate from the lysozyme/TAG peptide fused scFv (D1.3) surface was measured.

EXAMPLE 5

Cloning expression and purification of antibody-calmodulin fusions

In the work described in this example, calmodulin is fused to a recombinant protein and this is a target for a peptide ligand. Calmodulin fusions are purified by affinity and ion exchange chromatography.

Cloning.

We constructed an expression vector that allows cloning of the desired gene (in our case recombinant antibody fragments) into restriction sites in the vector polylinker, appends at the C-terminal extremity a gene coding for residues 2–149 of *Xenopus laevis* calmodulin (which encodes the same protein sequence as human calmodulin) and directs the expression of the resulting chimaeric protein into the periplasmic space of *E.coli* cells.

The gene for the *Xenopus laevis* calmodulin (Chien, Y. & Dawid, I. (1984) *Mol. Cell. Biol.* 4, 507–513; provided by C. Klee) was amplified by PCR (1 min at 94° C., 1 min. at 60°

C. and 2 min at 72° C. for 25 cycles) using the primers 5' AGT TCC GCC ATA GCG GCC GCT GAC CAA CTG ACA GAA GAG CAG 3' (SEQ ID NO: 16) and 5' ATC CAT CGA GAA TTC TTA TCA CTT TGA TGT CAT CAT TTG 3' (SEQ ID NO: 17) to append a NotI site, two stop codons and an EcoRI site. The product was digested with NotI and EcoRI, and cloned into pHEN1 (Hoogenboom, H. R., et al. (1991) *Nucl. Acids Res.*, 19, 4133–4137) to give the pDN152. The genes encoding the scFv antibody fragments HyHEL-10 (anti-lysozyme; Lavoie T. B., et al. (1992) *J. Immunol.* 148, 503–513) and MFE-23 (anti-carcinoembryonic antigen, anti-CEA; Chester, K. A., et al. (1994) *Lancet* 343, 455–456) were subcloned into the Sfi1/ Not1 sites of pDN152, to give pDN162 and pDN154, respectively, which were transformed into *E. coli* TG1 (Gibson T J (1984) University of Cambridge) for expression of soluble antibody and purification (see below). The anti-lysozyme antibody fragment scFv D1.3 was also subcloned into pDN152.

Further single chain Fv fragments have been cloned into pDN152, expressed and purified. These are a scFv fragment derived from a hybridoma expressing B1, a murine monoclonal antibody that is an anti-idiotype to the surface Ig of the lymphoma BCL-1 (J. Brissinck et al *J. Immunol.* 147 4019–4026, 1991) and 225–28S a scFv fragment directed against melanoma cells.

Expression, detection and purification of calmodulin fusion proteins.

Cultures of TG1 harbouring pDN154 or pDN162 were grown at 37° C. overnight (in 2× TY, 100 μg/ml ampicillin, 1% glucose), diluted 1:100 in fresh medium (2× TY, 100 μg/ml ampicillin, 0.1% glucose) to $A^{600}$=0.8, induced at 22° C. with 1 mM IPTG and grown overnight. Culture supernatants and periplasms were prepared as described by Schmidt and Skerra (1993; supra) and assayed by ELISA. 96 wells plates (Falcon) were first coated with purified CEA (10 μg/ml in PBS; gift of J. Embleton) or hen egg lysozyme (3 mg/ml in PBS; Sigma) overnight and then blocked with 2% milk powder in PBS (200 μl/well 2 hs). 100 μl of antibody calmodulin fusion was added to each well, followed by 15 μl anti-calmodulin Fab fragment DN169/F3 (Griffiths, A. D., et al. (1994). Isolation of high affinity human antibodies directly from large synthetic repertoires. *EMBO J.*, in the press; 50 μg/ml) and 15 μl anti-human $C_k$ horseradish peroxidase conjugate (The Binding Site; 1:40 dilution) in 2% milk powder in PBS. After incubation at room temp for 15 min, the plate was washed 4 times with PBS and developed with BM-Blue (Boehringer Mannheim) chromogenic substrate.

Purification of MFE23-calmodulin fusion

The 50 ml periplasmic extract from a 1 liter culture of pDN154 was made up to 20 mM $CaCl_2$ and affinity purified. The sample was loaded on a 3 ml column of N-(6-aminohexyl)-5-chloro-1-naphtalenesulfonamide-agarose (Sigma) in TBSC (TBS+1 mM $CaCl_2$), and washed with TBSC+0.5 M NaCl. The sample was eluted with 20 mM EGTA, and made up to 50 mM $CaCl_2$. Alternatively, the periplasmic extract was filtered and purified by ion exchange (in the absence of calcium) by FPLC using a MONO-Q 5/5 anion exchange chromatography column, washing with TBS and eluting with TBS and a NaCl gradient (0 to 1M). The fusion protein eluted at 0.5 M NaCl. The expression level and the purification yields were checked by 20% SDS polyacrylamide PHAST gel (Pharmacia).

Expression and purification of scFvHyHEL10-calmodulin fusion protein.

Figure 2:
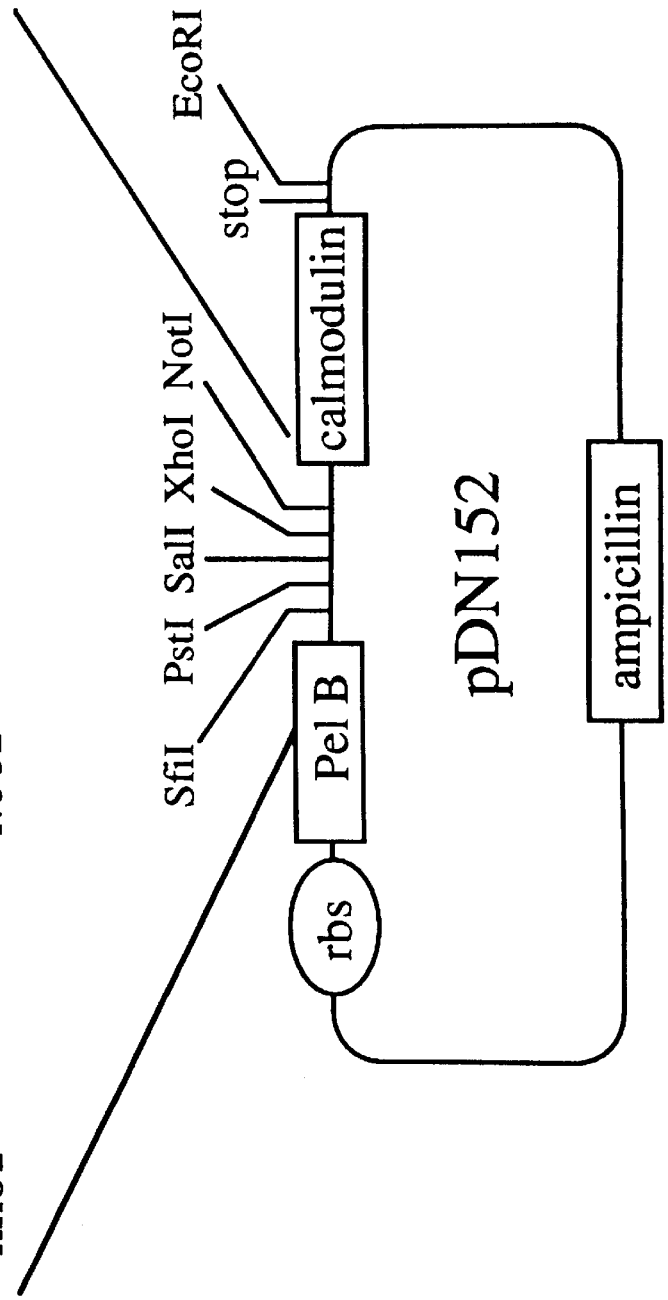
FIG. 2: Cloning vector pDN152 for the expression of the scFv-CAL fusions. rbs, ribosome binding site; Pel B, leader sequence.
Figure 3:
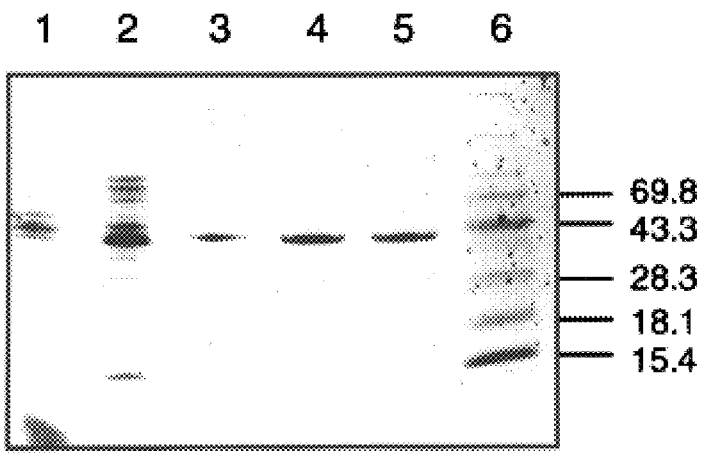
FIG. 3: Purification of scFv-CAL fusions. Lanes: (6) markers (Sigma); (1) supernatant HyHEL-10; (2) periplasmic MFE-23; (3) HyHEL-10 purified on HEL-SEPHAROSE chromatography column (4) MFE-23 purified on N-(6-aminohexyl)-5-chloro-1-naphtalene-sulfonamide-agarose; (5) MFE-23 purified on MONO-Q anion exchange column.

The gene encoding the scFv fragment of the anti-lysozyme antibody HyHEL-10 (Lavoie et al., 1992; supra) was cloned into a vector (pDN152) to append the calmodulin gene as described above and give the clone pDN162 (FIG. 2), and the fusion protein expressed by secretion from bacteria. The formation of active antibody could be assayed by the presence of a positive ELISA signal. The fusion protein could be purified from the culture broth or from periplasmic lysates by affinity chromatography on HEL-SEPHAROSE chromatography media (Ward et al, supra). The yield of the fusion protein from shaker flasks was about 15 mg/l culture (FIG. 3), similar to the levels of expression of the scFv fragment (not shown).

The fusion protein could also be purified to homogeneity with similar yields in a single step using the calmodulin ligand N-(6-aminohexyl)-5-chloro-1-naphtalenesulfonamide-agarose (binding with calcium, eluting with EGTA), or by anion-exchange chromatography (using FPLC on a column of MONO-Q anion exchange resin (Pharmacia).

These experiments indicate the utility of calmodulin tags for affinity purification, and suggest that both the antibody and calmodulin moiety were folded and functional.

Expression and purification of scFvD1.3-calmodulin fusion protein.

The single chain FvD1.3-calmodulin fusion was shown to bind lysozyme by the ELISA procedure above. Surface plasmon resonance analysis of scFv(D1.3)-calmodulin fusion protein binding to lysozyme was performed on a BIAcore machine (Pharmacia), immobilizing 2000 RUs lysozyme on a microsensor chip, subsequently injecting scFv(D1.3)-calmodulin supernatant and observing specific binding to the chip and an off rate of 0.003 $s^{-1}$ typical of the D1.3 antibody.

The chimaeric antilysozyme antibody scFv (D1.3) fused to calmodulin was purified to homogeneity using either a lysozyme-SEPHAROSE affinity column or a N-(6-aminohexyl)-5-chloro-1-napthalenesulfonamide-agarose resin. In the latter case purification was easy and mild. Periplasmic extracts containing scFv(D1.3)-calmodulin, washing with TBS with 1 mM $CaCl_2$ (TBSC), then with TBSC plus 400 mM NaCl and finally eluting with TBS with 20 mM EGTA. The product was pure as judged by SDS-PAGE and gave rise to a band in native gels which was shifted by the addition of an excess of lysozyme to the sample. Typically, several milligrams of fusion protein were obtained from 1 liter of culture.

Thus, fusions of calmodulin with single chain Fv fragments can be readily expressed and purified under mi d conditions.

EXAMPLE 6

Determination of dissociation properties of calmodulin with fluorescent peptides and detection of calmodulin with fluorescent peptides.

We created fluorescent peptide ligands of calmodulin by modifying mastoporan (SEQ ID NO: 6), a peptide that binds calmodulin with high affinity ($K_d$=3×10$^{-10}$ M; Malencik and Anderson, 1983; supra; the sequence of mastoporan was extended at both the N- and C-terminus (Table 2; SEQ ID NOS: 9–11), and an N-terminal cysteine residue introduced for labelling with iodoacetamidofluorescein. The synthesis of the fluorescent peptides was as described in example 2.

Figure 4:
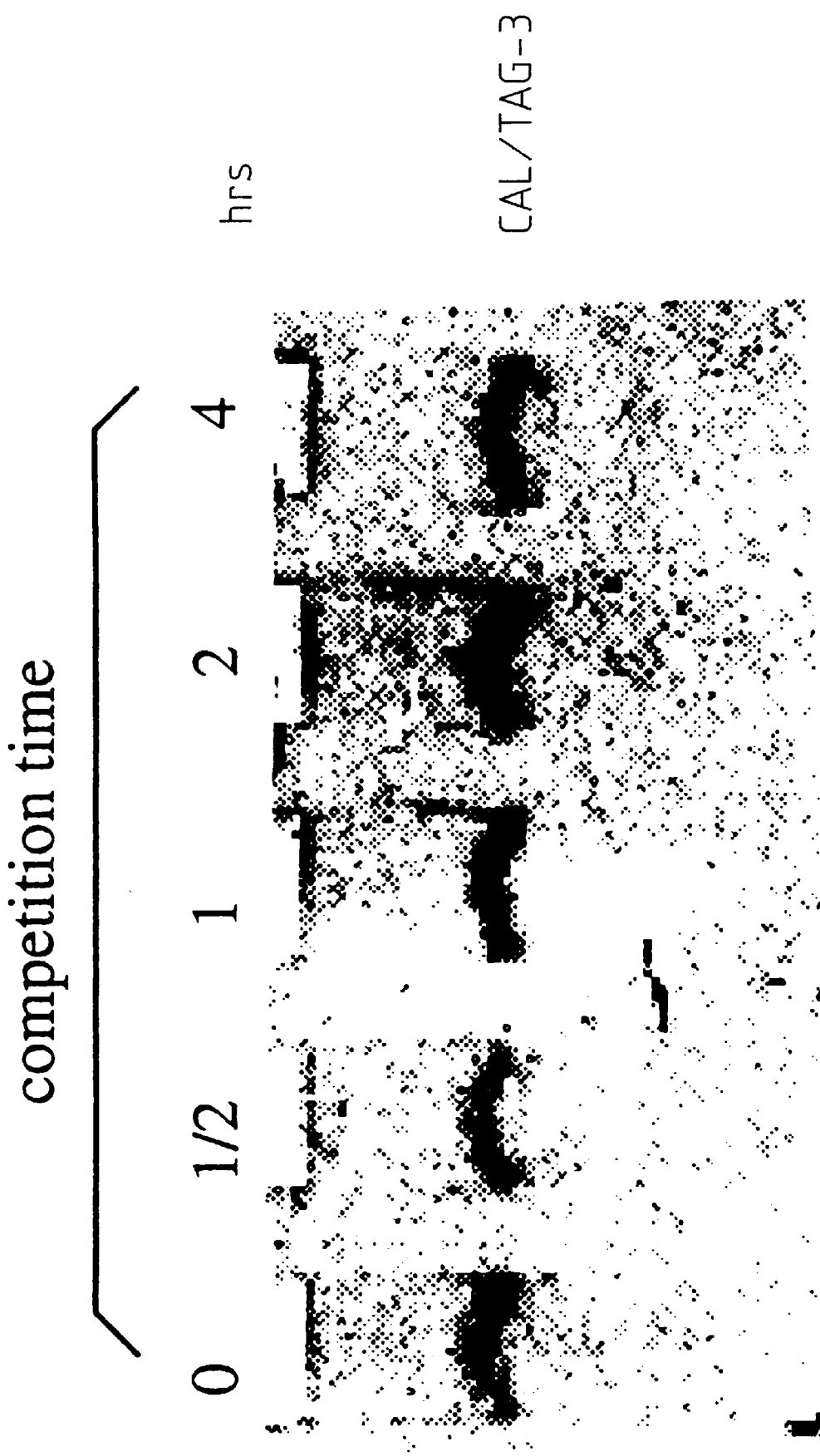
FIG. 4: Dissociation of peptide ligands from calmodulin. 600 nM calmodulin was pre-mixed in TBSC and 10% sucrose with 50 nM fluorescein-labeled TAG3 peptide. Aliquots were incubated on ice with a large excess (7 $\mu$M) unlabeled peptide for 0, 0.5, 1, 2, and 4 hrs, and analysed on a native 15% polyacrylamide gel (as in Laemmli, 1970 supra except with $CaCl_2$ to 1 MM) in a Hoefer Mighty Small apparatus, and imaged with a cooled CCD-camera based fluorescent gel imaging system developed in collaboration with Confocal Technologies (Liverpool, UK) and Digital Pixel (Brighton, UK).

The fluorescent peptides were shown to form stable complexes with calmodulin (FIG. 4), with slow off-rates. 600 nM calmodulin was pre-mixed in TBSC and 10% sucrose with 50 nM fluorescein-labeled TAG3 peptide. Aliquots were incubated on ice with a large excess (7 $\mu$M) unlabelled peptide for 0, 0.5, 1, 2, and 4 hrs, and analysed on a native 15% polyacrylamide gel (as in Carr & Scott, 1992 supra) except with $CaCl_2$ to 1 mM) in a Hoefer Mighty Small apparatus, and imaged with a cooled CCD-camera based fluorescent gel imaging system developed in collaboration with Confocal Technologies (Liverpool, UK) and Digital Pixel (Brighton, UK).

Thus, when the complex of calmodulin with fluorescent TAG3 peptide was incubated with a large excess of unlabelled peptide, and the mixtures analysed on a native polyacrylamide gel using a fluorescent gel imager, the fluorescent peptide was not significantly displaced from the calmodulin even after four hours competition.

EXAMPLE 7
Use of antibody-calmodulin fusions in band shift assays

The scFv-calmodulin fusions HyHEL-10 and MFE23 generated above with specificity for lysozyme and CEA respectively were shown to bind to their antigens by ELISA and were then shown to be effective in band shift assays.

The fluorescent peptides generated in example 2 were then used to detect the formation of antigen-antibody complexes. Thus hen egg lysozyme (HEL) was added to the fluorescently labelled anti-lysozyme scFv (HyHEL-10)-calmodulin fusion, and the mixtures were analysed by gel electrophoresis. The peptides could be used to fluorescently label single chain Fv fragment-calmodulin (scFv-CAL) fusions from both purified preparations or periplasmic extracts (FIG. 5) to give a bandshift assay.

1 $\mu$l of periplasmic extracts or purified antibody were incubated with 1 $\mu$l of 10 $\mu$M fluorescinated TAG-3 peptide, 8 $\mu$l TBSC or with 8 $\mu$l 100 $\mu$M antigen solution in TBSC. The samples were run on a Homogeneous 20 PHAST Gel (Pharmacia) using native buffer strips, and the gel imaged. Lanes: (1) periplasm extract MFE-23-CAL; (2) purified MFE-23-CAL; (3) purified MFE-23-CAL and CEA; (4) purified MFE-23-CAL and HEL; (5) periplasm extract HyHEL-10-CAL; (6) purified HyHEL-10-CAL; (7) purified HyHEL-10-CAL and HEL; (8) purified HyHEL-10-CAL and CEA.

Figure 5:
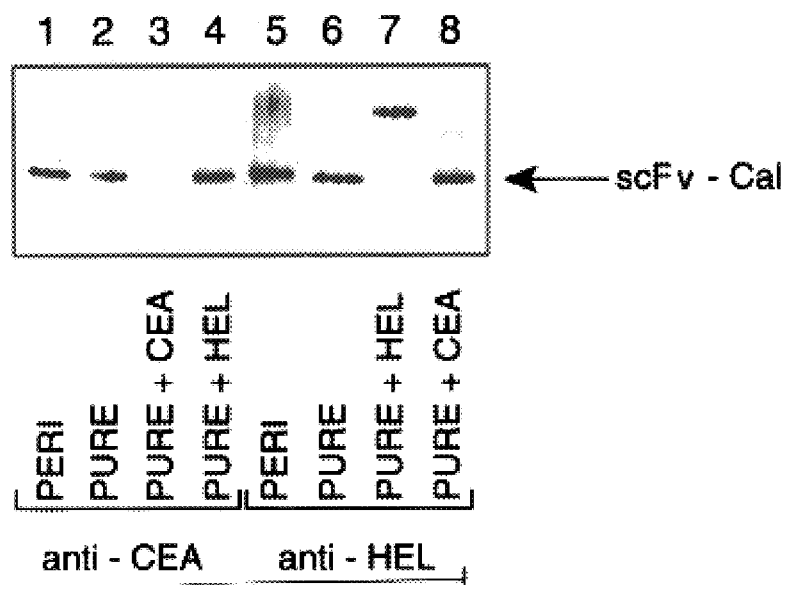
FIG. 5: Binding of scFv-CAL fusions to antigen by fluorescent band shift assay. 1 $\mu$l of periplasmic extracts or purified antibody were incubated with 1 $\mu$l of 10 $\mu$M fluorescinated TAG-3 peptide, 8 $\mu$l TBSC or with 8 $\mu$l 100 $\mu$M antigen solution in TBSC. The samples were run on a Homogeneous 20 Phast Gel (Pharmacia) using native buffer strips, and the gel imaged. Lanes: (1) periplasm extract MFE-23; (2) purified MFE-23; (3) purified MFE-23 and CEA; (4) purified MFE-23 and HEL; (5) periplasm extract HyHEL-10; (6) purified HyHEL-10; (7) purified HyHEL-10 and HEL; (8) purified HyHEL-10 and CEA (see below for details).

A "band shift" was seen, indicating formation of a complex; the completeness of the shift at concentrations of HEL>Kd for scFv (HyHEL-10) indicates that all of the fusion (as detected with the fluorescent peptide) binds to HEL. As expected, a band shift was not detected on adding HEL to a fluorescent calmodulin fusion (anti-CEA scFv (MFE-23)) with different antigen specificity (FIG. 5). However the band did shift on adding the cognate CEA; indeed the band disappeared entirely, presumably due to the high molecular weight (and aggregation) of CEA.

It is of interest that both scFv-calmodulin fusions and the complex with lysozyme move towards the anode, even with highly basic antigens such as HEL. Complex formation could even be detected using calmodulin fusions in bacterial extracts (FIG. 5). However the antigen-antibody complexes presumably need to be stable (as with HyHEL-10 and MFE-23), with half-lives longer than the time taken for gel electrophoresis (15 min). The half-life of the complexes between calmodulin and peptide tags are well in excess of that needed for the native gel electrophoresis.

EXAMPLE 8

Use of antibody-calmodulin fusions in confocal microscopy and FACS studies

Figure 6A:
FIG. 6A: Binding of scFv (MFE-23)-CAL fusions to cell surface antigen by confocal fluorescence laser microscopy. LOVO cells (surface CEA) incubated with TAG3 peptide (SEQ ID NO: 10) in complex with scFv (MFE-23)-CAL.
Figure 7A:
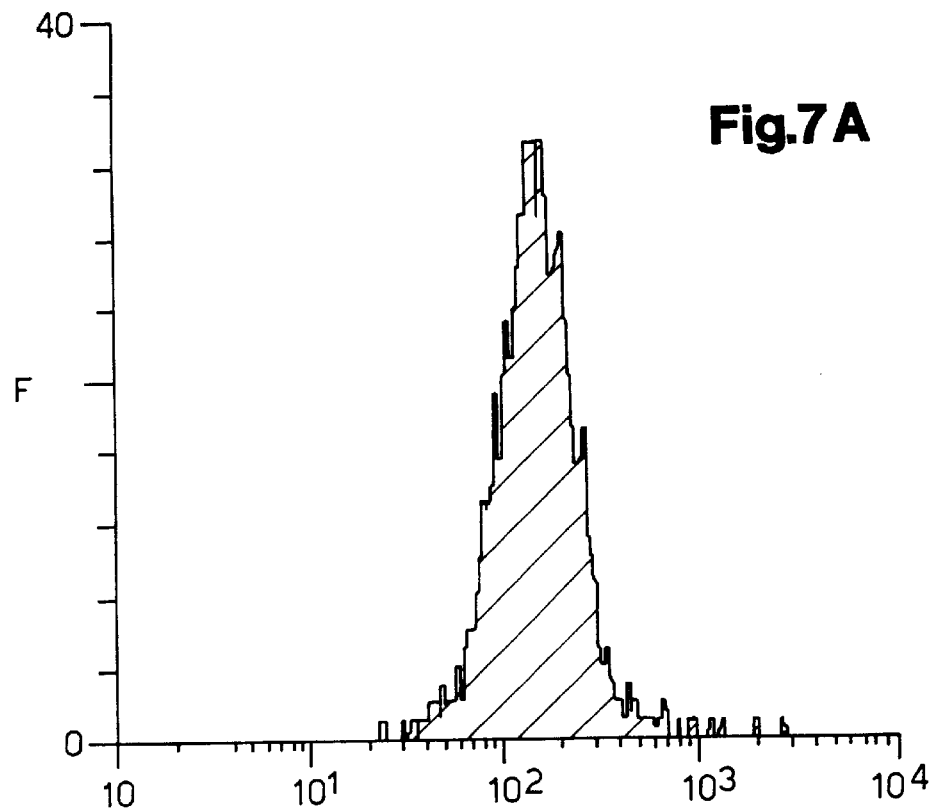
FIG. 7A: Binding of scFv (MFE-23)-CAL to MKN45 cells (surface CEA) detected by FACS using fluorescein-labeled TAG3 peptide (SEQ ID NO: 10).

The fluorescent antibody-calmodulin fusions could also be used as immunological reagents; the scFv(MFE-23)-calmodulin fusion was also used to detect CEA on the surface of a cell line LOVO by confocal laser microscopy (FIG. 6A), and by FACS analysis with the cell line MKN45 (FIG. 7A).

Cell targeting

Figure 6B:
FIG. 6B: Binding of scFv (HyHEL-10)-CAL fusions to cell surface antigen by confocal fluorescence laser microscopy. LOVO cells (surface CEA) incubated with TAG3 peptide (SEQ ID NO: 10) in complex with scFv (HyHEL-10)-CAL.

Confocal Laser Microscopy was used to study the use of calmodulin fusions in cell targeting. LOVO cells (ATCC designation CCL 229), expressing the carcinoembryonic antigen (CEA) on their membrane, were grown on microscope glass cover slips using RPMI and 10% fetal calf serum as culture medium. When the cells had grown almost to confluence the cover slips were immersed in acetone, then washed with TBSC and incubated with scFv(MFE-23)-calmodulin periplasmic extracts or with TBSC (negative control) for 30 minutes. The cover slips were then washed for 1 minute with TBSC, then incubated with fluorescinated peptide TAG-3 (1 $\mu$M; see Table 2) for 2 minutes, finally washed for 2 minutes with TBSC and analysed with an MRC-600 confocal laser microscope. FIGS. 6A and 6B shows binding of scFv-CAL fusions to cell surface antigen by confocal fluorescence laser microscopy. LOVO cells (expressing surface CEA) were incubated with TAG3 peptide in complex with (a) scFv(MFE-23)-CAL or (b) scFv (HyHEL-10)-CAL. FIG. 6A shows that binding occurs when the LOVO cells are incubated with TAG-3 peptide in complex with scFv (MFE-23)-CAL, which has specificity for CEA. FIG. 6B shows that no binding occurs when the cells are incubated with TAG-3 peptide in complex with scFv (HyHEL-10)-CAL which does not have specificity for CEA.

FACS.

Figure 7B:
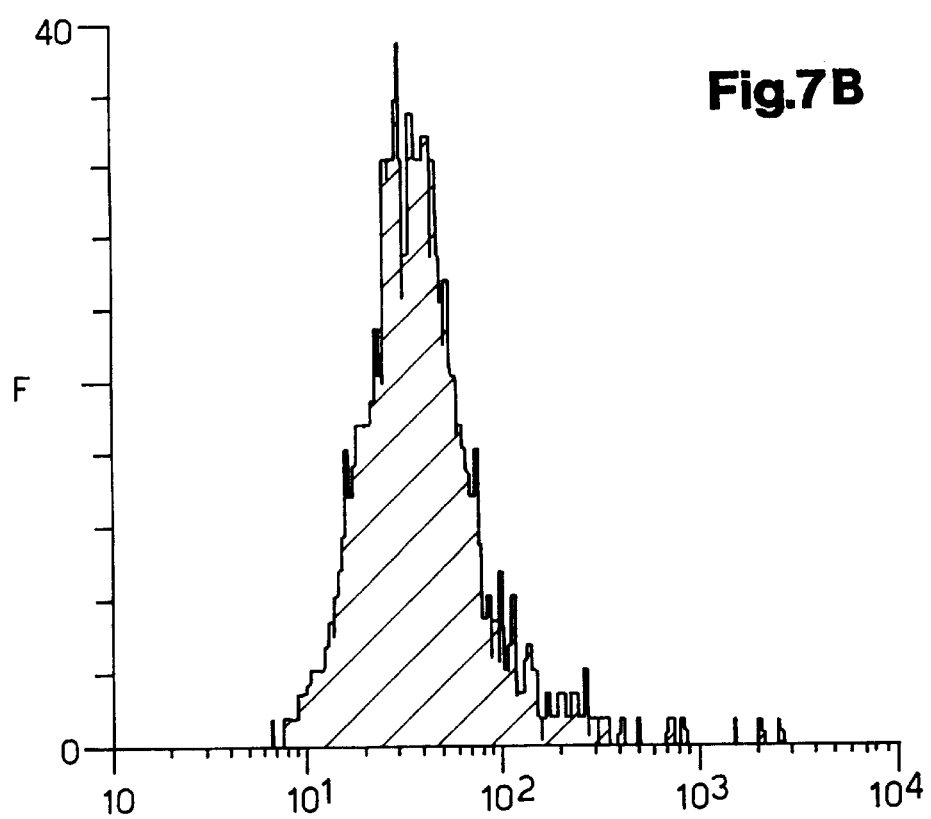
FIG. 7B: Binding of scFv (HyHEL-10)-CAL to MKN45 cells (surface CEA) detected by FACS using fluorescein-labeled TAG3 peptide (SEQ ID NO: 10).

MKN45 cells (gift from J. Embleton), expressing CEA on their membrane, were grown using RPMI, 10% fetal calf serum as culture medium. Cells were detached form the flask after 20 min. incubation in PBS, 2 mM EDTA with a cell scraper, centrifuged (10 min, 800 rpm) and resuspended in TBSC at a final concentration of $10^6$ cells/ml. 5 $\mu$l fluoresceinated TAG3 peptide ($10^{-5}$ M) were added to 50 $\mu$l antibody-calmodulin fusion ($10^{-5}$ M scFv(HyHEL-10)-CAL; or 2× $10^{-6}$ M scFv(MFE-23)-CAL), and after five mins the cells (500 $\mu$l) were added and incubated on ice for 20 min. The cells were then centrifuged (5 min, 1200 rpm), resuspended in 1 ml TBSC and analysed on a Becton & Dickinson FACScan. FIGS. 7A and 7B show binding of scFv-CAL to MKN45 cells (surface CEA) detected by FACS using fluorescein-labeled TAG3 peptide: (7A) scFv (MFE-23)-CAL; (7B) scFv(HyHEL-10)-CAL.

EXAMPLE 9
Assembly of bifunctional antibody-calmodulin fusions

The interaction of calmodulin and peptide suggests a means of assembling bifunctional macromolecules, as illustrated here by appending the peptide ligand as a tag to the C-terminus of the maltose binding protein (MBP). The maltose binding protein (MBP) gene was cloned into a pUC119-derived cytoplasmic expression vector (pDN124), which appends the TAG1 peptide (SEQ ID NO: 9) (and the protein purified on amylose resin).

Figure 8A:
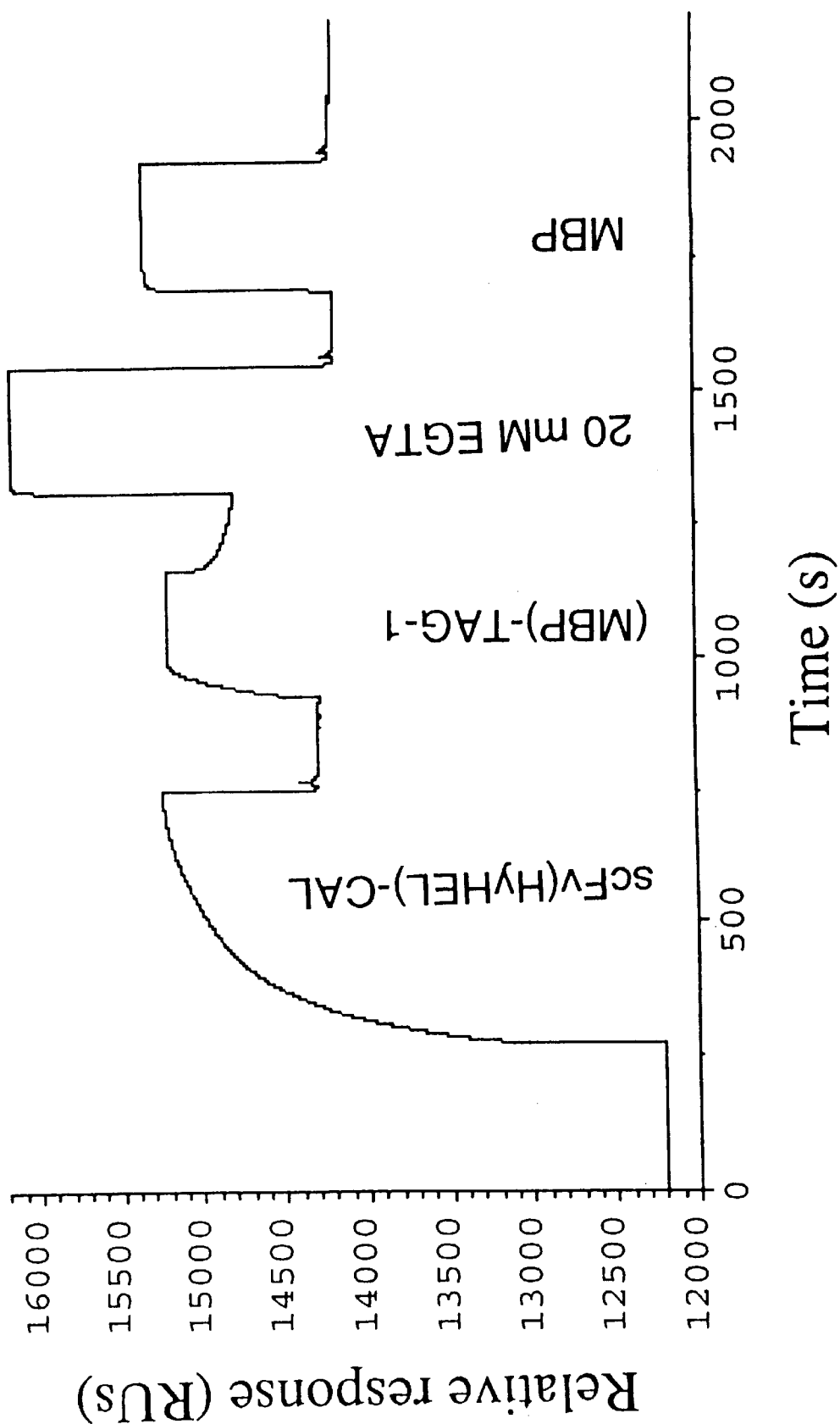
FIG. 8A: Binding of scFv-CAL and MBP-TAG1 detected by surface plasmon resonance (Pharmacia Biacore). 2500 resonance units (RUs) of turkey egg lysozyme (TEL) (Sigma) were immobilized on a microsensor chip of a BIAcore machine (Pharmacia). A solution of scFv(HyHEL-10)-TAG1 (5 μg/ml) in TBSC was injected onto the chip (flow rate 5 μl/min), followed by injections of MBP-TAG1 (5 μg/ml), then 20 mM EGTA (to dissociate the complex) and then MBP (New England Biolabs 5 μg/ml).
Figure 8B:
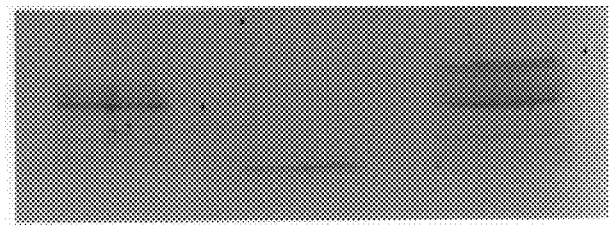
FIG. 8B: Homogeneous 20 Native Phast Gel (Pharmacia) for the analysis of scFv(HyHEL-10)-CAL and MBP-TAG1 interaction. Conditions as in FIG. 5, except the gel was stained with Coomassie. Lanes: 1, MBP-TAG1 (0.3 mg/ml); 2, scFv (HyHEL-10)-CAL (0.08 mg/ml); 3, scFv (HyHEL-10) (0.08 mg/ml)+MBP-TAG1 (0.3 mg/ml). The scFv (HyHEL-10) band shows retarded mobility upon addition of an excess of MBP-TAG1.

After expression in bacteria, and purification on an amylose affinity column, the tagged MBP was shown to interect with antibody calmodulin fusion using surface plasmon resonance (Jonsson. U., et al. (1991) *BioTechniques* 11, 620–627). Thus HEL was immobilised on the microsensor chip, and the chip saturated with with scFv(HyHEL-10)-CAL. The tagged MBP (but not MBP alone) was shown to bind to the chip, and could be dissociated by addition of EGTA (FIGS. 8A and 8B). The scFv calmodulin fusion and tagged MBP were also able to form a stable complex as shown by gel electrophoresis (not shown).

FIG. 8A. shows binding of scFv-CAL and MBP-TAG1 detected by surface plasmon resonance (Pharmacia Biacore). 2500 resonance units (RUs) of turkey egg lysozyme (TEL) (Sigma) were immobilised on a microsensor chip of a BIAcore machine (Pharmacia). A solution of scFv(HyHEL-10)-TAG1 (5 μg/ml) in TBSC was injected onto the chip (flow rate 5 μl/min), followed by injections of MBP-TAG1 (5 μg/ml), then 20 mM EGTA (to dissociate the complex) and then MBP (New England Biolabs 5 μg/ml). The scFv calmodulin fusion (scFv-CAL) and the tagged MBP (MBP-TAG1) were also able to form a stable complex as shown by gel electrophoresis (FIG. 8B). FIG. 8B shows a Homogeneous 20 Native Phast Gel (Pharmacia) for the analysis of scFv(HyHEL-10)-CAL and MBP-TAG1 interaction. Conditions were as in Example 7 and FIG. 5, except the gel was stained with Coomassie. Lanes: 1, MBP-TAG1 (0.3 mg/ml); 2, scFv (HyHEL10)-CAL (0.08 mg/ml); 3, scFv (HyHEL-10) (0.08 mg/ml)+MBP-TAG1 (0.3 mg/ml). The scFv (HyHEL10) band shows retarded mobility upon addition of an excess of MBP-TAG1.

EXAMPLE 10
Band shift assays using alternative fusion partners to the complete calmodulin molecule In order to be a suitable fusion partner for use in a bandshift assay, a molecule or a fragment of a molecule must have a high affinity for the ligand (eg tag peptide) and an off-rate low enough that the complex remains intact throughout the electrophoresis. In order to define further the types of calcium-binding proteins which may be used in these off-rate studies, in this example the properties of fragments of calmodulin and of the homologous calcium binding protein troponin C were examined.

C-terminal fragments of calmodulin (amino-acids 81 to 149 (SEQ ID NO: 20)) and N-terminal fragments (amino acids 1 to 80) were fused to single chain Fv D1.3 (anti-lysozyme) and expressed essentially as in Example 5. 1 μl of purified scFv (D1.3)-CAL (Example 5), scFv(D1.3)-CAL (N-domain), scFv(D1.3)-CAL(C-domain), calmodulin or troponin C were incubated with 10 μM fluoresceinated TAG-3 peptide and 8 μl TBSC. The samples were run on a High-Density Phast Gel (Pharmacia) using native buffer strips, and gel imaged. Complex formation with TAG-3, shown by detection of a fluorescent band, was observed for all the proteins except for scFv(D1.3)-CAL(N-domain).

Thus the C-terminal domain of calmodulin and troponin C are both potential fusion partners for the analysis of the affinity behaviour of a member of a specific binding pair.

EXAMPLE 11
Assessment of melatonin as a potential detection molecule for calmodulin-fusion molecule The high affinity of melatonin for calmodulin ($K_d$=188 pM) suggested it might be a useful detection molecule for fusions of calmodulin with recombinant proteins.

In order to assess this, 1 μl calmodulin (1 mg/ml) was incubated with 1 μCi 2-[$^{125}$I]-melatonin in 9 μl TBSC and run on a 15% polyacrylamide gel. The gel was as the running gel of Laemmli (*Nature* 1970 220 680–685), but with 0.5 mM $CaCl_2$ and no SDS in both gel and buffer. The gel was then autoradiographed, but no radioactive band was detected, indicating that the complex dissociates too rapidly, in line with the published half-life of the calmodulin-melatonin complex (120 s; Benitez-King et al., 1993).

Thus the half-life of the detection complex is a crucial parameter in determining the suitability of a fusion partner and a labelling tag, especially for use in a band-shift assay.

TABLE 1

Sequences and affinities of calmodulin-binding peptides

| NAME | | Kd |
|---|---|---|
| Ca++ pump | QILWFRGLNRIQTQIRVVNAFRSS-$NH_2$ (SEQ ID NO: 1) | 10 nM |
| SK-MLCK | KRRWKKNFIAVSAANRFKKISSSGAL (SEQ ID NO: 2) | 1 nM |
| Melittin | GIGAVLKVLTTGLPALISWIKRKRQQ (SEQ ID NO: 3) | 3 nM |
| Mastoparan X | INWKGIAAMAKKLL-$NH_2$ (SEQ ID NO: 4) | 1 nM |
| Mastoparan Polist. | VNWKKIGQHILSVL-$NH_2$ (SEQ ID NO: 5) | 4 nM |
| Mastoparan | INLKALAALAKKIL-$NH_2$ (SEQ ID NO: 6) | 0.3 nM |
| NO-30 | KRRAIGFKKLAEAVKFSAKLMGQAMAKRVK-$NH_2$ (SEQ ID NO: 7) | 2 nM |
| AC-28 | IKPAKRMKFKTVCYLLVQLMHCRKMFKA-$NH_2$ (SEQ ID NO: 8) | 2 nM |

TABLE 2

Sequences of calmodulin-binding TAG peptides

| mastoparan | INLKALAALAKKIL-$NH_2$ (SEQ ID NO: 6) |
|---|---|
| TAG 1 | C-EIKRAAA-INLKALAALAKKIL-$NH_2$ (SEQ ID NO: 9) |
| TAG 2 | C-EIKRAAA-INLKALAALAKKIL-OH (SEQ ID NO: 9) |
| TAG 3 | C-EIKRAAA-INLKALAALAKKIL-IKRKRQQ-$NH_2$ (SEQ ID NO: 10) |
| TAG 4 | C-EIKRAAA-INLKALAALAKKIL-IK-OH (SEQ ID NO: 11) |

Synthetic peptides derived from mastoparan that bind to calmodulin. For the TAG3 peptide, a sequence derived from melittin (which also binds to calmodulin) was incorporated in addition.

What is claimed is:

1. A molecule comprising (i) a fist polypeptide able to bind a ligand of calmodulin with a binding affinity which is dependent on calcium ion concentration, and (ii) a second polypeptide comprising a binding domain of an immunoglobulin member of a specific binding pair (sbp).

2. A molecule according to claim 1 wherein the first polypeptide is able to bind the ligand with a binding affinity with a calcium-dependent dissociation constant ($K_d$) of 10 nM or less, measured at a pH of between 6 and 9 at 20° C.

3. A molecule according to claim 2 wherein said dissociation constant is 1 nM or less.

4. A molecule according to claim 1 wherein the ligand is a polypeptide.

5. A molecule according to claim 4 wherein the ligand is mastoparan (SEQ ID NO: 6) or a polypeptide derivative of mastoparan that retains an ability of mastoparan to bind calmodulin with a binding affinity which is dependent on calcium ion concentration.

6. A molecule according to claim 1 wherein the first polypeptide and the ligand bind with a half-life of at least about 15 minutes.

7. A molecule according to claim 1 wherein the first polypeptide has a negative charge at about pH 8 of at least −5.

8. A molecule according to claim 7 wherein the first polypeptide has negative charge at about pH 8 of at least −10.

9. A molecule according to claim 1 wherein the first polypeptide is selected from the group consisting of calmodulin, troponin C and fragments and derivatives thereof that retain the ability to bind the ligand of calmodulin.

10. A molecule according to claim 1 wherein said polypeptides are fused together via a peptide bond.

11. A molecule according to claim 1 wherein the first polypeptide further comprises a label.

12. A molecule according to claim 11 wherein the label is fluorescent.

13. A multimer comprising:
(a) a first molecule which is a molecule according to claim 1 and
(b) a second molecule which comprises a polypeptide fusion of a ligand for the first polypeptide of the first molecule and another polypeptide,
the first and second molecules being non-covalently bound together via binding of the first polypeptide of the first molecule to the ligand.

14. A multimer according to claim 13 wherein said ligand comprises mastoparan (SEQ ID NO. 6) or a polypeptide derived from mastoparan, that retains the ability of mastoparan to bind the first polypeptide.

15. A multimer according to claim 13 which has a half-life of multimerisation of 15 minutes or more.

16. A molecule comprising a calmodulin-binding polypeptide, which is mastoparan (SEQ ID NO: 6) or a polypeptide derived from mastoparan, which has the ability to bind calmodulin and another polypeptide.

17. A molecule according to claim 16 wherein the calmodulin-binding polypeptide has an amino acid sequence which is INLKALAALAKKIL-CONH$_2$ (SEQ ID NO: 6),
C-EIKRAAA-INLKALAALAKKIL-COOH (SEQ ID NO: 9),
C-EIKRAAA-INLKALAALAKKIL-CONH$_2$ (SEQ ID NO: 9),
C-EIKRAAA-INLKALAALAKKIL-IKRKRQQ-CONH$_2$ (SEQ ID NO: 10),
C-EIKRAAA-INLKALAALAKKIL-IK-COOH (SEQ ID NO: 11)

or a derivative of any of these, which has the ability to bind calmodulin.

18. A molecule according to claim 16 wherein the other polypeptide comprises a binding domain of a member of a specific binding pair (sbp).

19. A molecule according to claim 18 wherein the binding domain is an immunoglobulin binding domain.

20. A molecule according to claim 16 wherein the calmodulin-binding polypeptide and the other polypeptide are fused together via a peptide bond.

21. A molecule according to claim 16 wherein the calmodulin-binding polypeptide is labelled.

22. A molecule according to claim 21 wherein the label is fluorescent.

23. A method of making the molecule according to claim 10, the method comprising a step of growing host cells containing nucleic acid encoding the molecule under conditions for expression of the molecule and a step of isolating the molecule by binding the first polypeptide to the ligand.

24. A method of isolating the molecule according to claim 1 comprising the steps of binding the molecule to said ligand to form a complex, and isolating the complex.

25. A method according to claim 24 further comprising an eluting step after said isolating step, to dissociate the molecule from the ligand.

26. A method according to claim 25 wherein the step of binding the molecule to said ligand occurs in the presence of calcium ions and the eluting step comprises sequestering calcium ions with a calcium sequestrant.

27. A method according to claim 24 wherein aid ligand comprises mastoparan or a polypeptide derivative of mastoparan that retains an ability of mastoparan to bind calmodulin with a binding affinity which is dependent on the calcium ion concentration.

28. A method according to claim 24 wherein the ligand comprises a label such that the ligand and the molecule form a labelled complex and wherein the step of isolating the complex includes detecting the label.

29. A method according to claim 28 wherein the label is fluorescent.

30. A method according to claim 24 wherein the isolation of the complex includes a step of ion exchange chromatography.

31. A method which comprises a step, following the step of isolating the molecule in accordance with claim 25, of cleaving the first polypeptide from the molecule.

32. A method according to claim 23 which comprises a step of eluting to dissociate the calcium-dependent binding molecule and the ligand.

33. A method which comprises a step, following making the molecule in accordance with claim 23 of cleaving the first polypeptide from the molecule.

34. A method which comprises the steps of binding a molecule according to claim 1 to said ligand to form a complex, isolating the complex, and cleaving the first polypeptide from the molecule.

35. A method of isolating a molecule according to claim 16 which comprises binding of the calmodulin-binding polypeptide to a polypeptide selected from the group consisting of calmodulin, troponin C, and a fragment or derivative thereof, that retains the ability to bind calmodulin-binding polypeptide.

36. A method according to claim 35 which comprises eluting to dissociate the calmodulin, troponin C, fragment or derivative thereof which retains the ability to bind calmodulin-binding polypeptide and the calmodulin-binding molecule.

37. A method which comprises a step, following isolation of the molecule comprising a calmodulin-binding polypeptide and another polypeptide in accordance with the method of claim 35 of cleaving the calmodulin-binding polypeptide from the molecule.

38. A method of labelling cells which comprises binding the molecule according to claim 11 to a complementary sbp member on the surface of the cells wherein the complementary sbp member is complementary to said second polypeptide.

39. A method of labelling cells which comprises the steps of binding a molecule according to claim 1 to a complementary sbp member on the surface of the cells, wherein the complementary sbp member is complementary to the second polypeptide, and contacting the cells with the ligand of said first polypeptide, wherein the ligand further comprises a label.

40. A method according to claim 39 wherein said ligand comprises mastoparan (SEQ ID NO: 6) or a polypeptide derivative of mastoparan that retains an ability of mastoparan to bind calmodulin with a binding affinity which is dependent on the calcium ion concentration.

41. A method according to claim 38 wherein the label is fluorescent.

42. A method which comprises sorting cells labelled by the method in accordance with claim 41 by fluorescent activated cell sorting (FACS).

43. A method of imaging cells comprising the steps of labelling the cells in accordance with claim 38 and detecting the label on the cells to provide an image of the cells.

44. A method of labelling cells which comprises binding a molecule according to claim 18 via its binding domain to complementary sbp member on the surface of the cells, the calmodulin-binding polypeptide of the molecule being labelled.

45. A method of labelling cells which comprises binding a molecule according to claim 18 via its binding domain to complementary sbp member on the surface of the cells and binding the calmodulin-binding polypeptide to labelled polypeptide selected from the group consisting of calmodulin, troponin C, and a fragment or derivative thereof, that retains the ability to bind calmodulin-binding polypeptide.

46. A method which comprises imaging cells labelled by a method in accordance with claim 44.

47. A band-shift assay method for determining binding affinity of said binding domain of said second polypeptide of the molecule according to claim 1 for a complementary sbp member, the method comprising binding the first polypeptide of the molecule to said ligand of calmodulin, wherein the ligand comprises a label, and comparing electrophoretic mobility of the resultant multimer in the presence and absence of the complementary sbp member.

48. A band-shift assay method for determining binding affinity of said binding domain of said second polypeptide of the molecule according to claim 2 for a complementary sbp member, the method comprising binding the first polypeptide of the molecule to said ligand of calmodulin, and comparing the electrophoretic mobility of the resultant multimer in the presence and absence of the complementary sbp member.

49. A band-shift assay method according to claim 38 wherein said dissociation constant is 1 nM or less.

50. A band-shift assay method according to claim 48 wherein the first polypeptide has a negative charge at pH 8 of at least −5.

51. A band-shift assay method according to claim 50 wherein the first polypeptide has negative change at about pH 8 of at least −10.

52. A band-shift assay method according to claim 48 wherein the first polypeptide and the ligand bind with a half-life of at least about 15 minutes.

53. A band-shift assay method according to claim 48 wherein the first polypeptide is selected from the group consisting of calmodulin, troponin C and fragments and derivatives thereof that retain the ability to bind the ligand of calmodulin.

54. A band-shift assay method according to claim 48 wherein said ligand comprises a fluorescent label.

55. A band-shift assay method for determining binding affinity of the binding domain of a molecule according to claim 18 for a complementary sbp member of interest, the method comprising binding the calmodulin-binding polypeptide of the molecule to labelled calmodulin, troponin C or a fragment or derivative thereof that retains the ability to bind calmodulin-binding polypeptide and comparing electrophoretic mobility of the resultant multimer in the presence and absence of the complementary sbp member.

56. A band-shift assay according to claim 55 wherein the label is fluorescent.

\* \* \* \* \*